(12) United States Patent
Maeda et al.

(10) Patent No.: US 10,417,931 B2
(45) Date of Patent: Sep. 17, 2019

(54) REHABILITATION ASSISTANCE DEVICE AND PROGRAM FOR CONTROLLING REHABILITATION ASSISTANCE DEVICE

(71) Applicant: Teijin Pharma Limited, Tokyo (JP)

(72) Inventors: Akihiro Maeda, Tokyo (JP); Fumi Fujita, Tokyo (JP); Hiroshi Kanatani, Tokyo (JP); Sunao Ikegawa, Tokyo (JP); Hironobu Kubo, Tokyo (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 22 days.

(21) Appl. No.: 15/322,628

(22) PCT Filed: Jul. 2, 2015

(86) PCT No.: PCT/JP2015/069144
§ 371 (c)(1),
(2) Date: Dec. 28, 2016

(87) PCT Pub. No.: WO2016/002885
PCT Pub. Date: Jan. 7, 2016

(65) Prior Publication Data
US 2017/0132947 A1    May 11, 2017

(30) Foreign Application Priority Data
Jul. 3, 2014 (JP) .................... 2014-137816

(51) Int. Cl.
*A63B 22/00*  (2006.01)
*A63B 23/00*  (2006.01)
(Continued)

(52) U.S. Cl.
CPC .......... *G09B 19/003* (2013.01); *A61B 5/1122* (2013.01); *A61B 5/1124* (2013.01);
(Continued)

(58) Field of Classification Search
CPC ................................................ A63B 2213/00
See application file for complete search history.

(56) References Cited

U.S. PATENT DOCUMENTS

2006/0079817 A1    4/2006  Dewald et al.
2006/0293617 A1*  12/2006  Einav .................. A61H 1/0274
                                                       601/33
(Continued)

FOREIGN PATENT DOCUMENTS

CN           1956692 A      5/2007
CN         102631277 B     12/2013
(Continued)

OTHER PUBLICATIONS

English-language Machine Translation of JP 2003-079683A publication, published Mar. 18, 2013, to Tsujio Shozo Kawahira Kazumi.
(Continued)

*Primary Examiner* — Omkar A Deodhar
(74) *Attorney, Agent, or Firm* — Sughrue Mion, PLLC

(57) ABSTRACT

A rehabilitation assistance device (1), provided with: an arm part (30) having a holding part (20) for holding a part of the upper limb or the lower limb of a user, the arm part (30) movably supporting the holding part (20); a memory unit (80) for storing training information, the memory unit (80) storing first training information defined in advance; a motion information acquisition unit (61) for acquiring motion information associated with the movement of the holding part (20), the motion information acquisition unit (61) acquiring first motion information for the holding part (20) moved on the basis of the first training information; a motion evaluation unit (72) for generating evaluation information in which the motion information is evaluated, the motion evaluation unit (72) evaluating the first motion information and generating first evaluation information; and
(Continued)

a display (40) for displaying at least one of the training information, the motion information, and the evaluation information.

17 Claims, 25 Drawing Sheets

(51) Int. Cl.
| A63B 21/00 | (2006.01) |
| G09B 19/00 | (2006.01) |
| A61H 1/02 | (2006.01) |
| G16H 40/63 | (2018.01) |
| G16H 50/30 | (2018.01) |
| G06F 3/033 | (2013.01) |
| A61B 5/11 | (2006.01) |
| A63B 24/00 | (2006.01) |
| G09B 5/02 | (2006.01) |
| A63B 71/06 | (2006.01) |
| A63B 21/005 | (2006.01) |
| A63B 23/035 | (2006.01) |
| A63B 23/12 | (2006.01) |
| G05G 9/047 | (2006.01) |
| G16H 20/30 | (2018.01) |
| A63B 69/00 | (2006.01) |
| A63B 26/00 | (2006.01) |
| A63B 71/00 | (2006.01) |
| A63B 23/14 | (2006.01) |

(52) U.S. Cl.
CPC ............. *A61H 1/02* (2013.01); *A61H 1/0277* (2013.01); *A61H 1/0281* (2013.01); *A63B 21/0058* (2013.01); *A63B 21/00178* (2013.01); *A63B 21/4035* (2015.10); *A63B 21/4049* (2015.10); *A63B 23/03508* (2013.01); *A63B 23/1209* (2013.01); *A63B 24/0062* (2013.01); *A63B 71/0622* (2013.01); *G05G 9/047* (2013.01); *G06F 3/033* (2013.01); *G09B 5/02* (2013.01); *G16H 20/30* (2018.01); *G16H 40/63* (2018.01); *G16H 50/30* (2018.01); *A61B 2505/09* (2013.01); *A61H 1/0285* (2013.01); *A61H 2201/1207* (2013.01); *A61H 2201/1635* (2013.01); *A61H 2201/1659* (2013.01); *A61H 2201/5007* (2013.01); *A61H 2201/5035* (2013.01); *A61H 2201/5038* (2013.01); *A61H 2201/5043* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01); *A61H 2203/0425* (2013.01); *A63B 21/00181* (2013.01); *A63B 21/4019* (2015.10); *A63B 21/4021* (2015.10); *A63B 23/14* (2013.01); *A63B 24/0087* (2013.01); *A63B 26/003* (2013.01); *A63B 69/0053* (2013.01); *A63B 69/0057* (2013.01); *A63B 71/0009* (2013.01); *A63B 2071/065* (2013.01); *A63B 2071/0647* (2013.01); *A63B 2071/0683* (2013.01); *A63B 2208/0228* (2013.01); *A63B 2220/10* (2013.01); *A63B 2220/16* (2013.01); *A63B 2220/20* (2013.01); *A63B 2220/30* (2013.01); *A63B 2220/40* (2013.01); *A63B 2220/51* (2013.01); *A63B 2220/803* (2013.01); *A63B 2225/20* (2013.01)

(56) References Cited

U.S. PATENT DOCUMENTS

| 2011/0004126 A1 | 1/2011 | Einav et al. |
| 2013/0171601 A1 | 7/2013 | Yuasa et al. |

FOREIGN PATENT DOCUMENTS

| JP | 9-120464 A | 5/1997 |
| JP | 11-333021 A | 12/1999 |
| JP | 2001-000420 A | 1/2001 |
| JP | 2002-177351 A | 6/2002 |
| JP | 2003-79683 A | 3/2003 |
| JP | 2006-192258 A | 7/2006 |
| JP | 2006-320424 A | 11/2006 |
| JP | 2007-50249 A | 3/2007 |
| JP | 2009-131647 A | 6/2009 |
| JP | 2012-157404 A | 8/2012 |
| WO | 2005074371 A2 | 8/2005 |
| WO | 2006/021952 A2 | 3/2006 |
| WO | 2009/104190 A2 | 8/2009 |
| WO | 2012/039467 A1 | 3/2012 |

OTHER PUBLICATIONS

International Search Report for PCT/JP2015/069144 dated Sep. 29, 2015 [PCT/ISA/210].
Communication dated May 16, 2017 from the European Patent Office in counterpart Application No. 15816031.7.
Communication dated Jun. 2, 2017 from the European Patent Office in counterpart Application No. 15 816 031.7.

* cited by examiner

REHABILITATION ASSISTANCE DEVICE AND PROGRAM FOR CONTROLLING REHABILITATION ASSISTANCE DEVICE

CROSS REFERENCE TO RELATED APPLICATIONS

This application is a National Stage of International Application No. PCT/PCT/JP2015/069144, filed on Jul. 2, 2015, which claims priority from Japanese Patent Application No. 2014-137816, filed on Jul. 3, 2014, the contents of all of which are incorporated herein by reference in their entirety.

TECHNICAL FIELD

The present invention relates to a rehabilitation support apparatus supporting rehabilitation of the upper extremities and lower extremities of patients and a control program of a rehabilitation support apparatus.

BACKGROUND ART

Rehabilitation aimed at restoration of motor functions to semi-impaired upper extremities and lower extremities of patients suffering from strokes etc. and assessment of motor functions in the process of rehabilitation are generally performed labor intensively by physical therapists or occupational therapists (below, referred to together as "therapists"). Therefore, there are limits to increasing efficiency in rehabilitation and assessment of motor functions by therapists.

For example, in rehabilitation of an upper extremity, mainly repeated accurate movement of the impaired upper extremity over a range of movement slightly broader than the current movable range of the joint, passively or actively, is sought as much as possible. That is, the therapist teaches the patient the accurate movement and manually applies a passive load mainly to the impaired upper extremity of the patient or guides active movement of the patient and makes the patient perform repetitive movement in a suitable range of movement to thereby try to restore the motor function.

In such rehabilitation, due to fatigue of the therapist or the upper limit on rehabilitation time in medical insurance systems, the number of times of movements which can be repeated by a therapist for restoration of motor functions and the time which he or she can devote for assessment of motor functions are limited. Further, rehabilitation is performed one-on-one by a therapist and patient, so depending on the experience or skill of the therapist, there is a possibility of differences or variation in the medical quality of the rehabilitation, that is, the extent of restoration of motor function. Therefore, rehabilitation support apparatuses for assisting training by therapists and standardizing medical quality have been proposed (for example, PLT 1 and PLT 2).

Each of the rehabilitation support apparatuses described in PLT 1 and PLT 2, for example, has a robot arm to which a forearm part of a semi-impaired upper extremity of a patient is fastened and a drive and control part for driving and controlling the movement of the robot arm. The rehabilitation is performed by moving the upper extremity of the patient fastened to the robot arm in accordance with instructions of the therapist. The movement of the upper extremity of the patient is detected by a sensor attached to the robot arm. The drive and control part drives the robot arm so as to guide movement of the upper extremity based on a training program set in advance by the therapist or drives the robot arm so as to apply a load to the movement of the upper extremity or switches these drive methods in accordance with the time or number of training operations. The rehabilitation support apparatus can support training for rehabilitation by therapists by such operations. Such rehabilitation support apparatuses are mainly installed in hospitals and other medical facilities and are used for hospitalized patients and outpatients under the guidance of the therapists.

CITATION LIST

Patent Literature

PLT 1. Japanese Patent Publication No. 2007-050249A
PLT 2: Japanese Patent Publication No. 2009-131647A

SUMMARY OF INVENTION

Technical Problem

On the other hand, in diagnosis and treatment under most insurance systems, rehabilitation is based on one-on-one treatment by a therapist and patient. Along with the increase in the population of senior citizens, the number of patients requiring rehabilitation will increase. It is expected that the number of therapists will become insufficient for this. Even if the above-mentioned such rehabilitation support apparatuses can be used as means for making rehabilitation more efficient, in the final analysis, the rehabilitation support apparatuses are used under the direction of therapists, so there is a possibility that these will not contribute to greater efficiency of therapists.

Almost all of the above-mentioned such rehabilitation support apparatuses were developed assuming mainly use under the direction of doctors, therapists, and other medical practitioners in hospitals and other medical facilities. Therefore, how to set the training programs of the rehabilitation support apparatuses is completely left to the judgment of the medical practitioners in charge. Further, setting the training programs so as to realize the optimum rehabilitation for the many types of conditions of patients is extremely complicated. Therefore, even medical practitioners find it difficult to suitably use rehabilitation support apparatuses for restoration of motor functions of patients.

Further, even patients who want to continue with rehabilitation for restoration of motor functions and maintenance of functions after discharge from the hospital, patients finding it difficult to commute to the hospital due to various situations, etc. should engage in rehabilitation continuously for a sufficient time. Accordingly, when a patient uses such a rehabilitation support apparatus for rehabilitation, a rehabilitation support apparatus which the patient can use autonomously or with the assistance of family etc. without guidance or supervision by medical practitioners or even in the absence of medical practitioners has been sought.

Furthermore, in the assessment of motor functions in rehabilitation, the medical practitioners act as assessors which render subjective judgments based on criteria for judgment determined for the different assessed items, so depending on the assessors, differences and variation arise in the results of assessment as well. Further, since the assessed content is large and complicated, there is also the problem that assessment of motor functions takes time.

The present invention provides, in one aspect, a rehabilitation support apparatus generating objective data indicators enabling medical practitioners and patients to easily understand the extent of recovery of motor functions. The present invention provides, in another aspect, a rehabilitation support apparatus utilizing objective data indicators and semi-automatically or automatically selecting suitable training programs in accordance with the conditions of patients.

Solution to Problem

According to the present invention, there is provided a rehabilitation support apparatus characterized by comprising an arm part having a holding part for holding part of an upper extremity or lower extremity of a user and supporting the holding part to be able to move, a storage part storing training information, which storage part storing predetermined first training information, a motion information acquiring part acquiring motion information accompanying movement of the holding part, the motion information acquiring part acquiring first motion information of the holding part moved based on the first training information, a motion assessing part generating assessment information assessing the motion information, the motion assessing part assessing the first motion information and generating first assessment information, and a display part displaying at least one of the training information, the motion information, and the assessment information.

The first training information, first motion information, and first assessment information are information which medical practitioners set and which are generated based on results of rehabilitation of patients when patients use the rehabilitation support apparatus for training.

Further, according to the present invention, there is provided a rehabilitation support apparatus wherein the motion assessing part generates the first assessment information based on a comparison of the first training information and the first motion information.

Furthermore, according to the present invention, there is provided a rehabilitation support apparatus further comprising a training information setting part generating next training information based on the assessment information and storing the training information in the storage part and, characterized by the training information setting part generating second training information based on the first assessment information and storing the second training information in the storage part. The second training information means training information when updating first training information and performing rehabilitation by the rehabilitation support apparatus of the present invention.

Furthermore, according to the present invention, there is provided a rehabilitation support apparatus wherein the motion information acquiring part acquires second motion information of the holding part moved based on the second training information, the motion assessing part assesses the second motion information to generate second assessment information, and the training information setting part generates second training information based on the first assessment information and/or the second assessment information.

The "second motion information" is motion information of the holding part moved based on the second training information, while the "second assessment information" is assessment information generated by assessing the second motion information. Further, the second training information generated after motion based on the second training information is generated based on the first assessment information, all of the assessment information (first assessment information and second assessment information), several of the second assessment information (for example, several recent second assessment information), immediately preceding second assessment information, etc.

Furthermore, according to the present invention, there is provided a rehabilitation support apparatus wherein the training information setting part generates the training information by selecting it from a predetermined plurality of the training information in the storage part.

Furthermore, according to the present invention, there is provided a rehabilitation support apparatus further comprising an interface part for entering initial assessment information on the motor functions of the user and, wherein the training information setting part generates the first training information based on the initial assessment information and stores the first training information in the storage part.

Furthermore, according to the present invention, there is provided a rehabilitation support apparatus wherein the display part displays the motion information in real time in accordance with movement of the holding part.

Further, according to the present invention, there is provided a rehabilitation support apparatus wherein the arm part has a support point at one end and can move with at least one degree of freedom from the support point.

Furthermore, according to the present invention, there is provided a rehabilitation support apparatus wherein the training information and the motion information include at least one among a position of the holding part, a movement time of the holding part, a speed of the holding part, an acceleration of the holding part, and a force applied to the holding part.

Furthermore, according to the present invention, there is provided a rehabilitation support apparatus further comprising an assessment information predicting part predicting assessment information to be reached by the user in the future based on a plurality of the assessment information of users and generating predicted assessment information.

Furthermore, according to the present invention, there is provided a rehabilitation support apparatus wherein the display part displays at least one of the training information, the assessment information, and the predicted assessment information.

Furthermore, according to the present invention, there is provided a rehabilitation support apparatus further comprising an assessment information converting part converting the assessment information to corresponding other assessment information or converting the corresponding other assessment information to the assessment information.

Furthermore, according to the present invention, there is provided a rehabilitation support apparatus wherein the other assessment information is shown by assessment items generally used in rehabilitation by Fugl-Meyer Assessment etc.

Furthermore, according to the present invention, there is provided a control program for a rehabilitation support apparatus comprising an arm part having a holding part of an upper extremity or lower extremity of a user and supporting the holding part to be able to move, which control program making the rehabilitation support apparatus perform a step of storing training information, which step storing predetermined training information, a step of acquiring motion information accompanying movement of the holding part, which step acquiring motion information of the holding part moved based on the training information, a step of generating assessment information assessing the motion information, which step assessing the motion information and generating assessment information, and a step of displaying at least one of the training information, the motion information, and the assessment information.

Advantageous Effects of Invention

According to the present inventions, the shared effects are exhibited of the provision of a rehabilitation support apparatus providing objective data indicators enabling an extent of restoration of motor functions to be easily understood by medical practitioners and patients. Further, the effect is exhibited of the provision of a rehabilitation support apparatus utilizing objective data indicators and selecting a suitable training program semi-automatically or automatically according to the condition of a patient.

DESCRIPTION OF EMBODIMENTS

Figure 1:
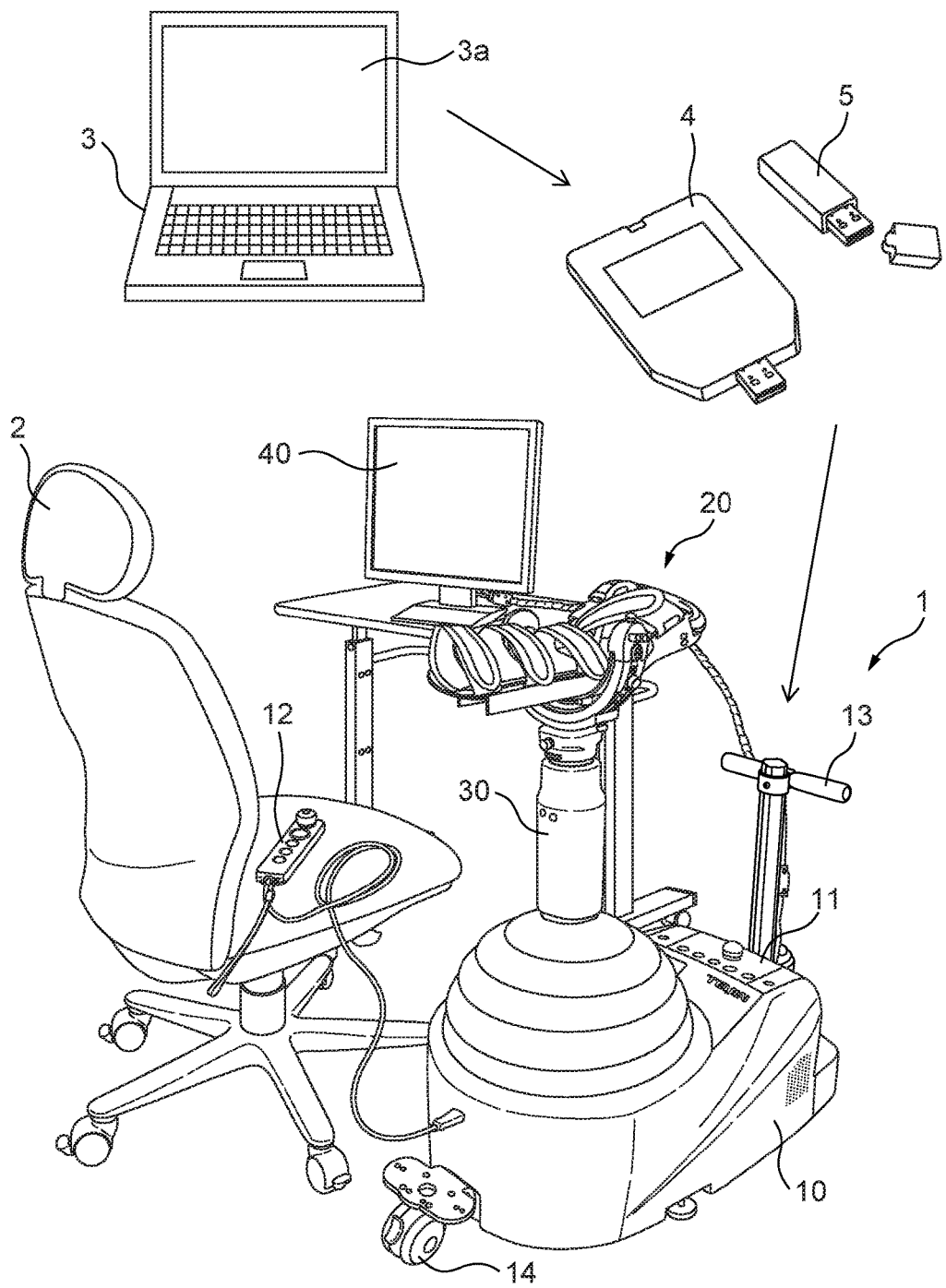
FIG. 1 is a perspective view of a rehabilitation support apparatus according to an embodiment of the present invention.

Below, referring to the drawings, embodiments of the present invention will be explained in detail. Note that, the scope of the present invention is not limited by these embodiments in any sense.

Figure 2:
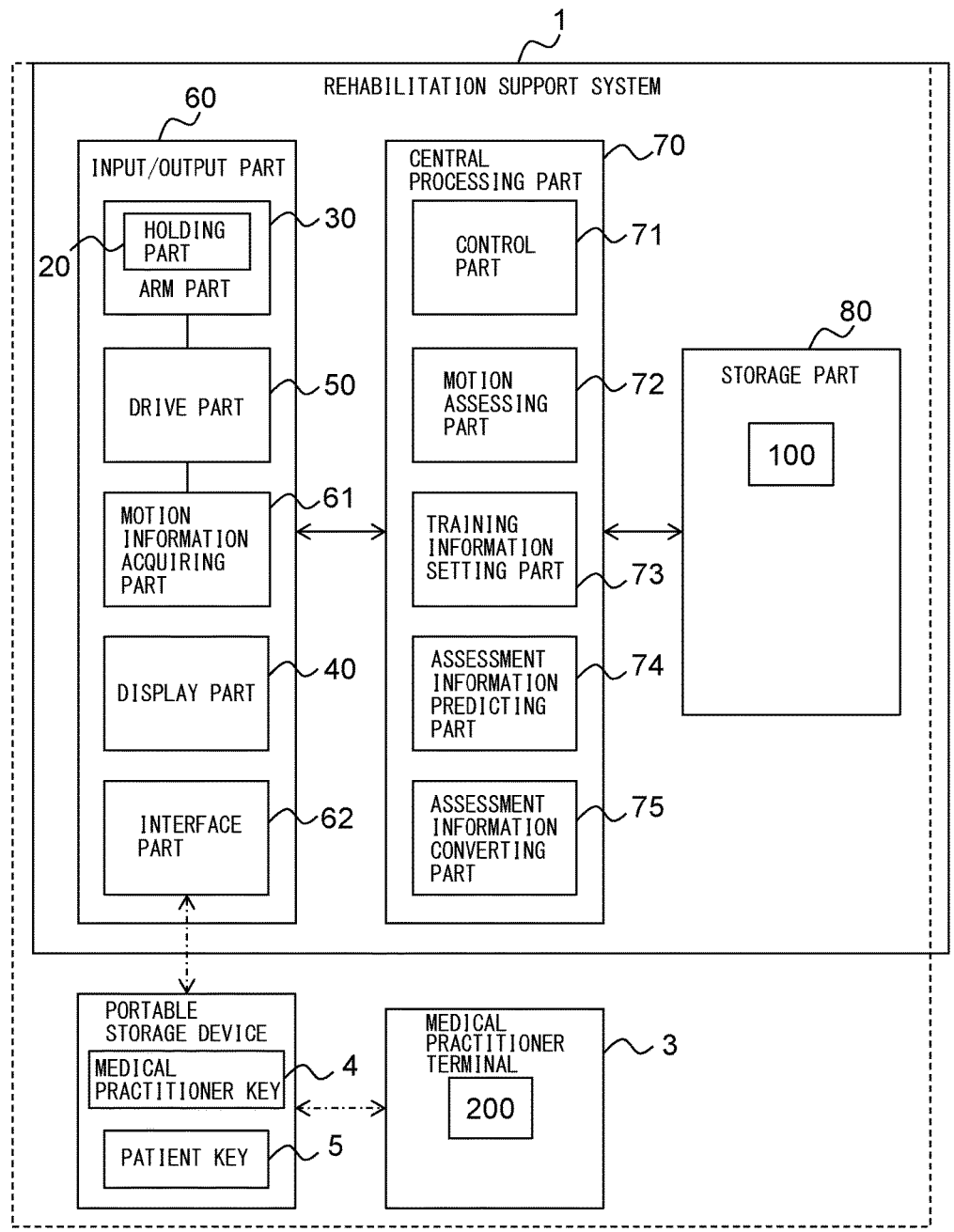
FIG. 2 is a block diagram showing the general configuration of a rehabilitation support apparatus.

FIG. 1 is a perspective view of a rehabilitation support apparatus 1 according to an embodiment of the present invention, while FIG. 2 is a block diagram showing the general configuration of the rehabilitation support apparatus 1. The rehabilitation support apparatus 1 according to the present embodiment is configured to deal with patients with impairment in one upper extremity.

The rehabilitation support apparatus 1 is used together with a patient chair 2. Further, a medical practitioner terminal 3 comprised of a personal computer or other data processing system for setting the rehabilitation support apparatus 1 and a medical practitioner key 4 and patient key 5 each comprised of a USB (Universal Serial Bus) memory or other portable storage device for transferring information between the rehabilitation support apparatus 1 and medical practitioner terminal 3 are used. Note that, the rehabilitation support apparatus 1 according to the present invention also includes the medical practitioner terminal 3, medical practitioner key 4, and patient key 5. In this case, it is also referred to as a "rehabilitation support system".

The rehabilitation support apparatus 1 has a main body 10, a holding part 20, arm part 30, display part comprised of the display 40, and drive part 50. Further, the rehabilitation support apparatus 1 has an input/output part 60, central processing part 70, and storage part 80.

The main body 10 has a front panel 11 provided with various types of lights showing the state of the rehabilitation support apparatus 1 and an emergency stop button, a controller 12 to be used by the patient, and a conveyance use handle 13 and casters 14. Further, the main body 10 has, as interface parts for the portable storage devices, USB slots (not shown) for insertion of the medical practitioner key and patient key (USB memory).

In the case of training for the right arm, as shown in FIG. 1, the chair 2 and display 40 are arranged at the left side from the rehabilitation support apparatus 1 so that the display 40 is arranged at the front of the patient. On the other hand, in the case of training for the left arm, the chair 2 and display 40 are arranged at the right side from the rehabilitation support apparatus 1. In the case of training for the right arm, the patient seated at the chair 2 fastens his right arm at the holding part 20 with the palm facing downward.

Figure 3:
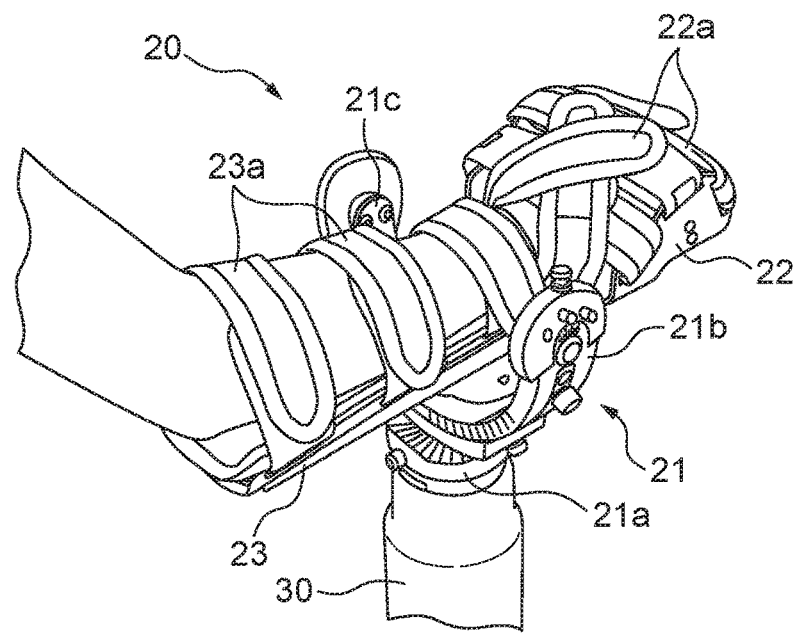
FIG. 3 is a perspective view of a holding part in a state of use.
Figure 4:
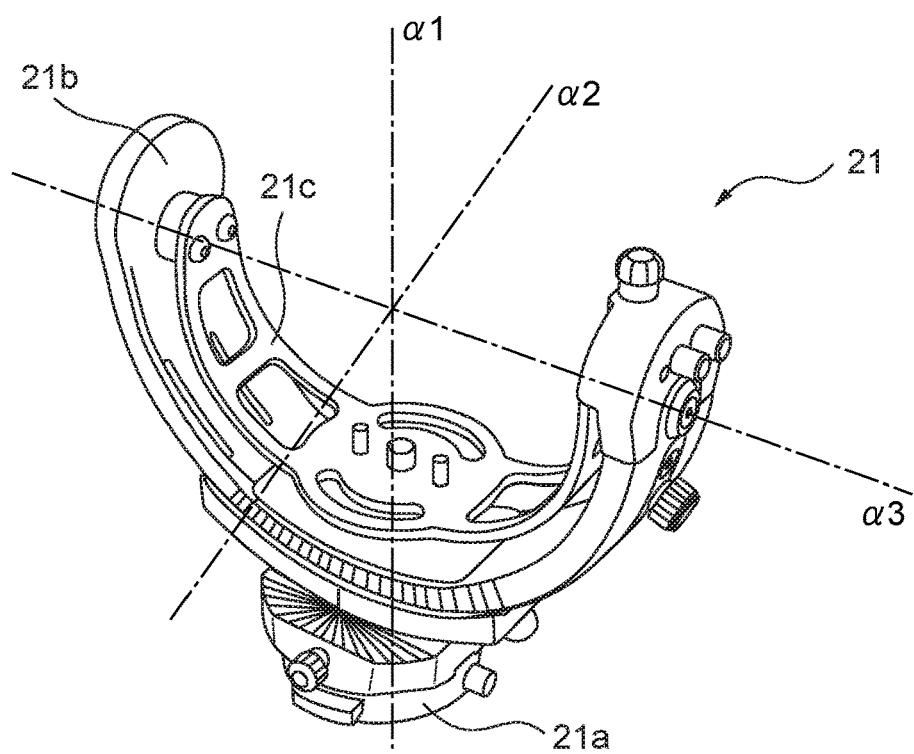
FIG. 4 is a perspective view of an attachment adapter of the holding part.

FIG. 3 is a perspective view of the holding part 20 in a state of use, FIG. 4 is a perspective view of an attachment adapter 21 of the holding part 20, and FIG. 5 is a view showing the operation of the holding part 20. The holding part 20 has the attachment adapter 21, a gripping member 22, and, if necessary, a forearm support member 23.

The attachment adapter 21 has an attachment part 21a, a semicircular arc shaped first swing member 21b, and a semicircular arc shaped second swing member 21c. The attachment part 21a is attached to the top end of the arm part 30 to be able to rotate about an axial line α1 matching the center axis of the arm part 30. The first swing member 21b is attached to the top surface of the attachment part 21a to be able to swing along the trajectory of that arc, that is, about the axial line α2 passing through the center of the circle including that arc. The second swing member 21c is arranged at the inside of the arc of the first swing member 21b, that is, at the upper side. The second swing member 21c is attached at the two ends of the arc to the two ends of the arc of the first swing member 21b to be able to rotate. Therefore, the second swing member 21c is attached to the first swing member 21b to be able to swing about the axial line α3 connecting the two ends.

The gripping member 22 is a plate shaped member supporting the hand of the patient and has a not shown grip which the patient grips and a fastening band 22a for fastening the hand of the patient. The forearm support member 23 is a plate shaped member supporting the forearm and is configured to be able to be lengthened or shortened in the length direction of the forearm in accordance with the condition or physical size of the patient. The forearm support member 23 has a fastening band 23a for fastening the forearm of the patient. At the end of the forearm support member 23, the gripping member 22 can be attached in a detachable manner.

Figure 5A:
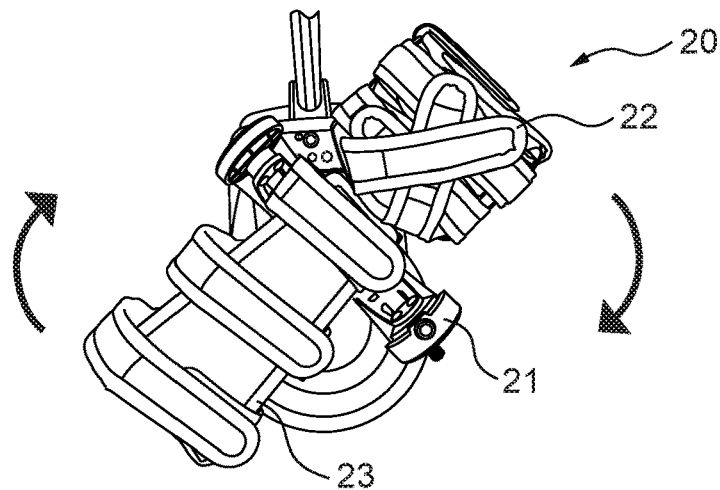
FIGS. 5A to 5C are views showing the operation of the holding part.
Figure 5B:
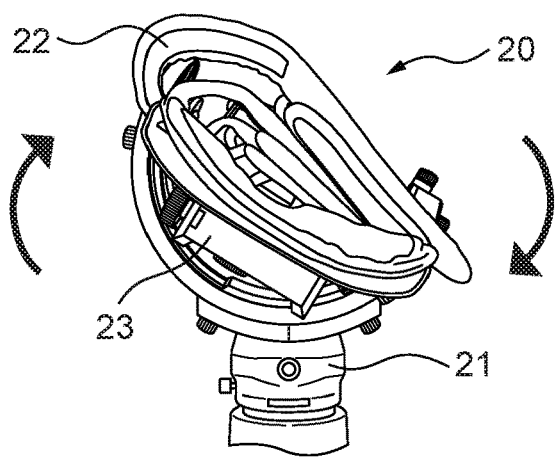
Figure 5C:
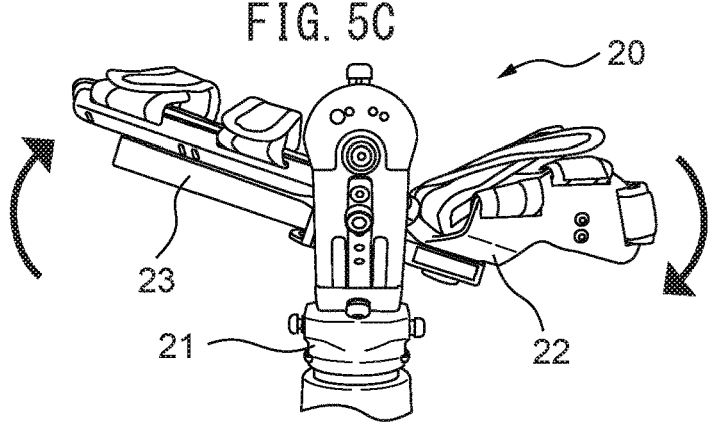

The gripping member 22 and forearm support member 23 are attached to the second swing member 21c of the attachment adapter 21. Therefore, the gripping member 22 and forearm support member 23 can rotate about the axial line α1 such as shown in FIG. 5A, swing about the axial line α2 such as shown in FIG. 5B, and swing about the axial line α3 such as shown in FIG. 5C. As a result, the holding part 20 passively operates in accordance with movement of the patient and will not obstruct movement of the patient.

Figure 6:
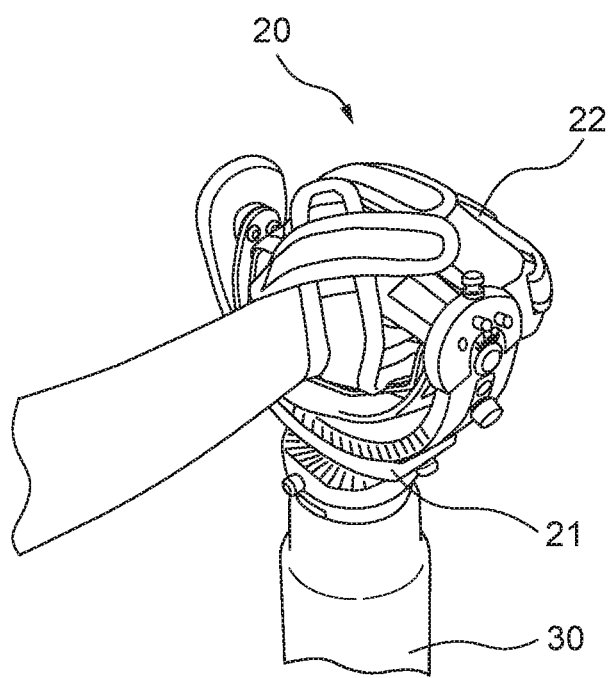
FIG. 6 is a perspective view of a holding part in another state of use.

Note that, FIG. 6 is a perspective view of the holding part 20 in another state of use. Depending on the condition of the patient, it is also possible not to use the forearm support member 23 but to attach only the gripping member 22 to the attachment adapter 21.

Figure 7:
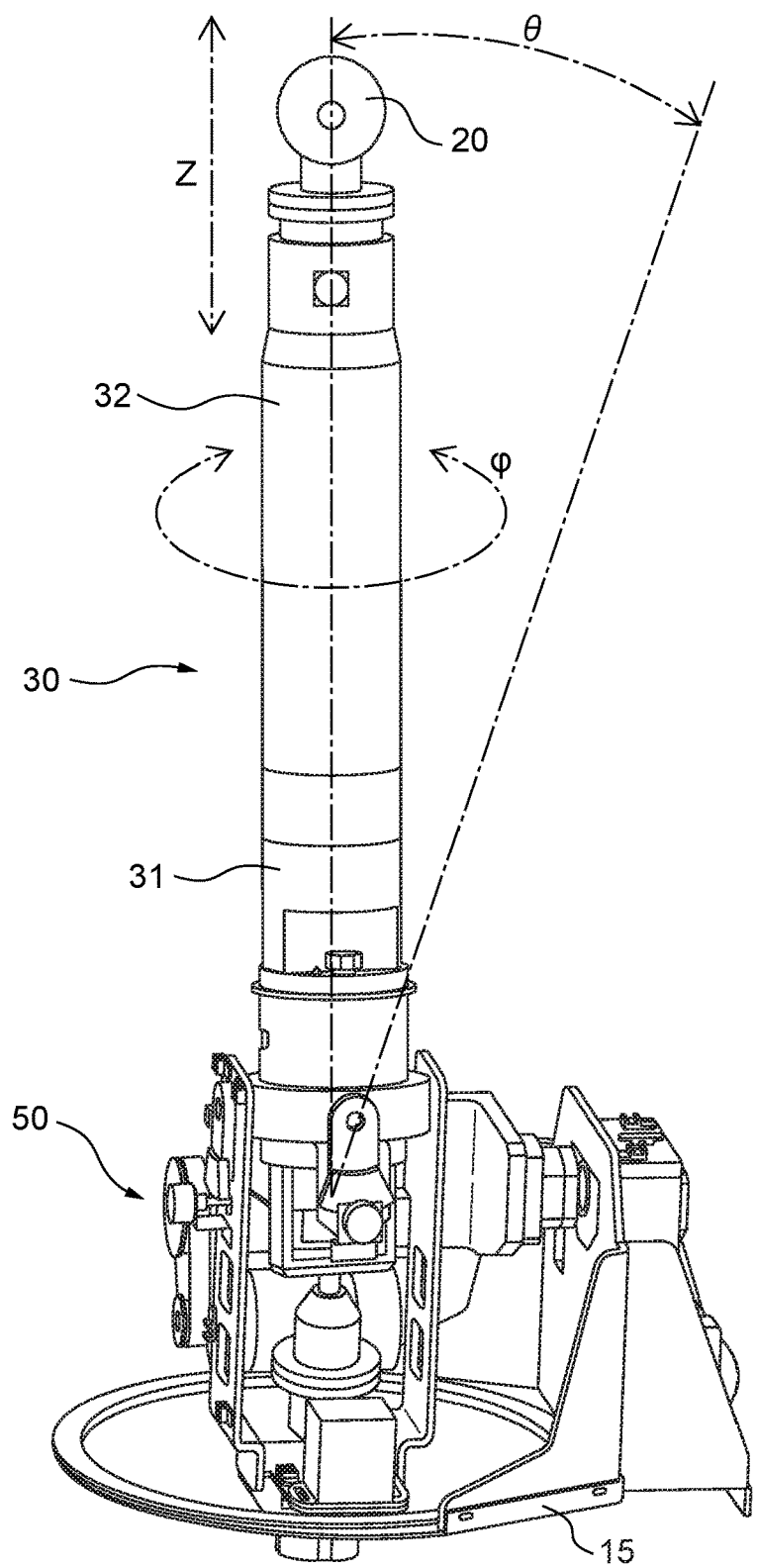
FIG. 7 is a perspective view of an arm part.
Figure 8:
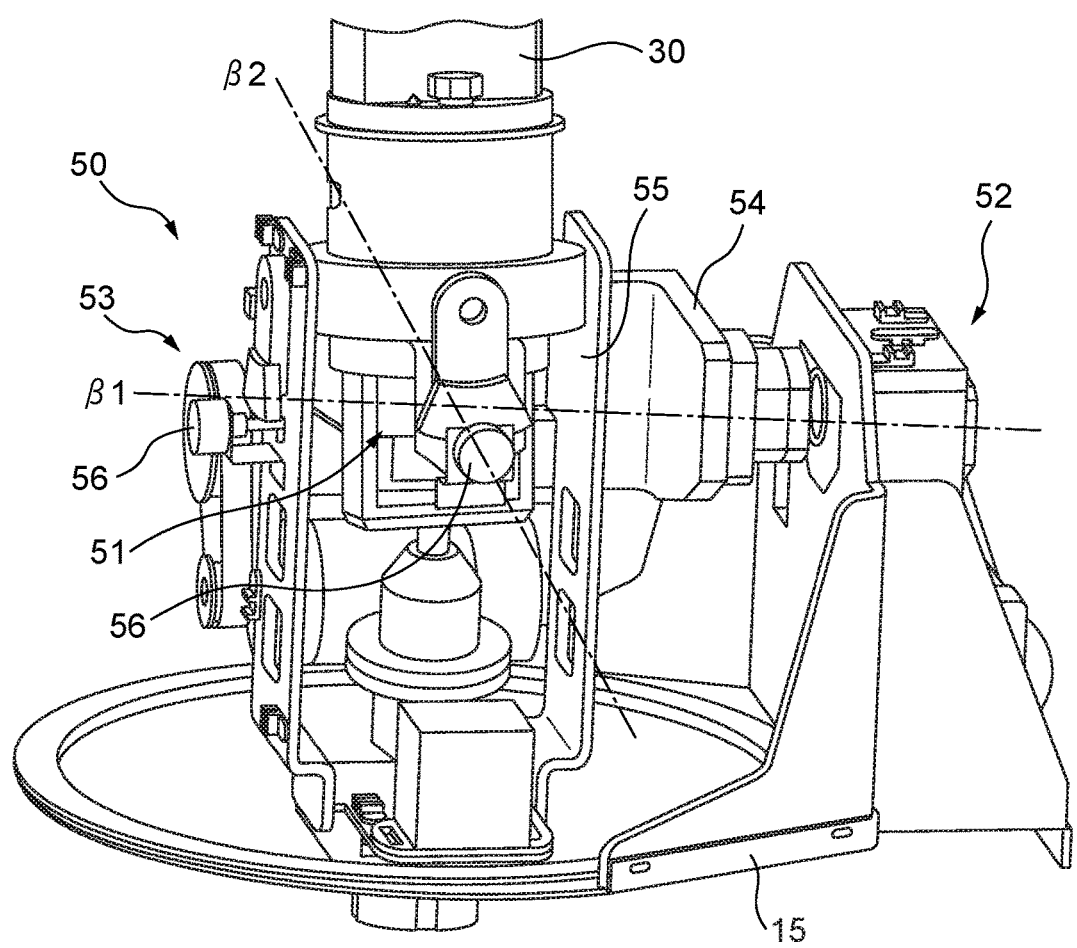
FIG. 8 is an enlarged perspective view of a drive part of the arm part.
Figure 9:
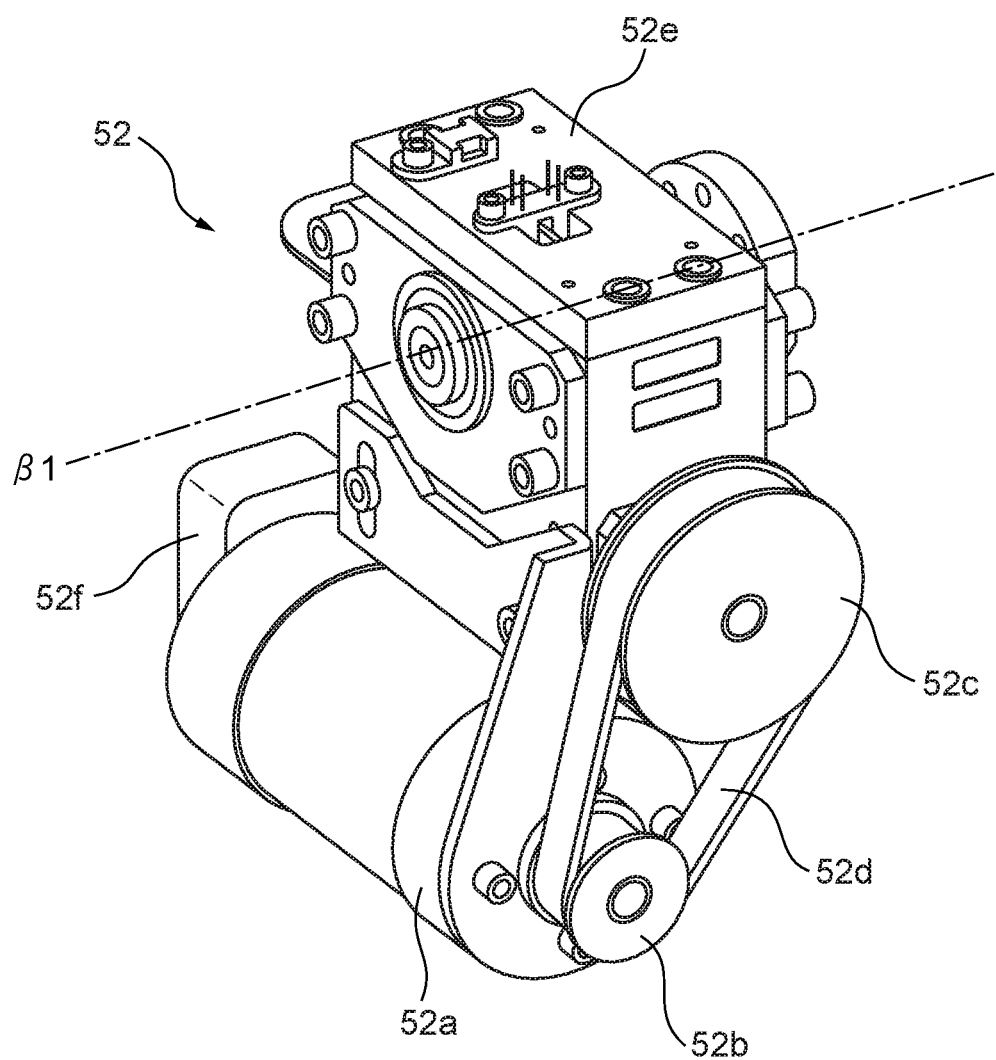
FIG. 9 is an enlarged perspective view of a first rotation drive unit of the arm part.

FIG. 7 is a perspective view of the arm part 30, FIG. 8 is an enlarged perspective view of a drive part 50 of the arm part 30, and FIG. 9 is an enlarged perspective view of a first rotation drive unit 52 of the arm part 30. Note that, in FIG. 7, a ball shaped holding part 20 different from the abovementioned holding part 20 is attached.

The arm part 30 is a columnar or bar-shaped mechanism. When not yet used, it is arranged so that its axial direction becomes parallel to the vertical direction. The arm part 30 has a fixed arm 31 arranged below and a movable arm 32 arranged above. The bottom end of the arm part 30, that is, the bottom end of the fixed arm 31, is supported by a drive part 50 arranged inside the main body 10. The top end of the arm part 30, that is, the top end of the movable arm 32, as explained above, has the holding part 20 attached to it in a detachable manner.

The drive part 50 has a linear drive unit 51, first rotation drive unit 52, second rotation drive unit 53, first arm frame 54, and second arm frame 55.

The linear drive unit 51 has a DC servo motor (not shown) and a linear movement mechanism (not shown) connected to the DC servo motor and extending inside the arm part 30. Due to the linear drive unit 51, the arm part 30 can be adjusted in length in the longitudinal direction or in height Z. That is, the linear drive unit 51 uses the DC servo motor to make the linear movement mechanism expand or contract and make the movable arm 32 move along the longitudinal direction through a nut or housing attached to the linear movement mechanism.

The first rotation drive unit 52 and the second rotation drive unit 53 have the same configurations. Therefore, while referring to FIG. 9, the first rotation drive unit 52 will be explained. The first rotation drive unit 52 has a DC servo motor 52a, a smaller diameter small pulley 52b, a larger diameter large pulley 52c, a belt 52d connecting the small pulley 52b and large pulley 52c, a gear mechanism 52e, and an encoder 52f.

The rotation by the DC servo motor 52a is transmitted to the gear mechanism 52e through the small pulley 52b, large pulley 52c, and belt 52d while reducing the rotational speed. The gear mechanism 52e has inside it a not shown worm gear. The rotational force transmitted by the DC servo motor 52a makes the worm having an axis of rotation parallel to the DC servo motor 52a rotate and makes the worm wheel engaging with the worm rotate about the axial line β1. The rotational angle of the DC servo motor 52a is detected by the encoder 52f. Similarly, the second rotation drive unit 53 makes the worm wheel rotate about the axial line β2.

The arm part 30 is attached to the second arm frame 55. The second arm frame 55 is attached through the second rotation drive unit 53 to the first arm frame 54. The first arm frame 54 is attached through the first rotation drive unit 52 to the fastening frame 15 of the main body 10. That is, the drive part 50 is attached to the main body 10 by being fastened to the fastening frame 15 of the main body 10.

Due to the arm part 30 and the drive part 50 having such configurations, the arm part 30 can operate like as if its lower end were attached to the main body 10 by a universal joint. That is, the arm part 30 can swing about the axial line β1 due to the first rotation drive unit 52 and can swing about the axial line β2 due to the second rotation drive unit 53. These swing motions can be performed independently. As a result, the arm part 30, in particular the holding part 20, can be made to move along any trajectory on the spherical surface by within a predetermined angular range. In other words, the holding part 20 can be made to move within a predetermined angular range independently in both the angle θ and angle φ directions in the spherical coordinate system such as shown in FIG. 7. Note that, the range of the angle φ is 0 degree to 360 degrees.

Furthermore, as explained above, the length Z in the longitudinal direction of the arm part 30 can be adjusted, so it is possible to arrange the holding part 20 at any position in the space of within the length Z-range of the arm part 30 within the angular range of the angle θ. Therefore, the rehabilitation support apparatus 1 according to the present embodiment enables training for rehabilitation in three dimensions (motion with 3 degrees of freedom).

The rehabilitation support apparatus 1 further has, in addition to the encoder 52f of the first rotation drive unit 52 and second rotation drive unit 53, a potentiometer 56 and other various types of sensors and can detect position, angle, force and pressure, time, etc. For example, the potentiometer 56 indirectly detects the load of the arm part 30 in swinging about the axial line β1 and the axial line β2. Specifically, the rotational angle is detected and the actual load is calculated in advance from the relationship between the linearly approximated rotational angle and corresponding load. By controlling the first rotation drive unit 52 and the second rotation drive unit 53 based on the results, it is possible to make the arm part 30 move so as to assist swinging of the arm part 30 or possible to make the arm part 30 move so as to provide resistance to swinging of the arm part 30, that is, so as to make the load felt by the patient increase. Further, the bottom end of the arm part 30 is surrounded by a not shown elastic member. Due to this, a predetermined load is generated for movement of the arm part 30 in all directions.

Referring to FIG. 2, the input/output part 60, the central processing part 70, and the storage part 80 of the rehabilitation support apparatus 1 will be explained.

The input/output part 60 has the above-mentioned holding part 20, arm part 30, display 40, drive part 50, motion information acquiring part 61, and interface part 62. The motion information acquiring part 61 has various types of sensors including the above-mentioned encoder 52f and potentiometer 56. The interface part 62 has an interface circuit for reading information in a medical practitioner key and patient key or other USB memory or writing information in the USB memory. Note that, the input/output part 60 may have a keyboard, mouse, or other input device.

The central processing part 70 has one or more processors and their peripheral circuits. The central processing part 70 comprehensively controls the overall operation of the rehabilitation support apparatus 1 and, for example, is a CPU (central processing unit). The central processing part 70 performs processing based on computer programs stored in advance in the storage part 80. The central processing part 70 has a control part 71, motion assessing part 72, training information setting part 73, assessment information predicting part 74, and assessment information converting part 75. These parts of the central processing part 70 are functional modules loaded by a program run on the processor of the central processing part 70. At the time of the run processing, the central processing part 70 receives signals from the input/output part 60 and sends signals to it. For example, the central processing part 70 sends control signals to the drive part 50 and receives their feedback signals and signals from various types of sensors. Note that, the medical practitioner terminal 3 may have the motion assessing part 72, training information setting part 73, assessment information predicting part 74, and assessment information converting part 75.

The storage part 80 has a RAM (random access memory), ROM (read only memory), or other memory device or a hard disk or other fixed disk device. In the storage part 80, the control program or other computer programs used for various types of processing in the rehabilitation support apparatus 1 (drive programs, operating system programs, application programs, etc.), a database, table, etc. are stored. The computer programs may be installed in the storage part 80 from, for example, a CD-ROM (Compact Disk Read Only Memory), DVD-ROM (Digital Versatile Disk Read Only Memory), or other computer readable portable recording medium using a known setup program etc.

Next, the training application program for using the rehabilitation support apparatus 1 will be explained.

The training application program is comprised of an apparatus application program 100 running on the rehabilitation support apparatus 1 and a terminal application program 200 running on the medical practitioner terminal 3. The apparatus application program 100 is stored in advance in the storage part 80. The terminal application program 200 uses the above-mentioned known setup program etc. for installation and use at the medical practitioner terminal 3.

Figure 10:
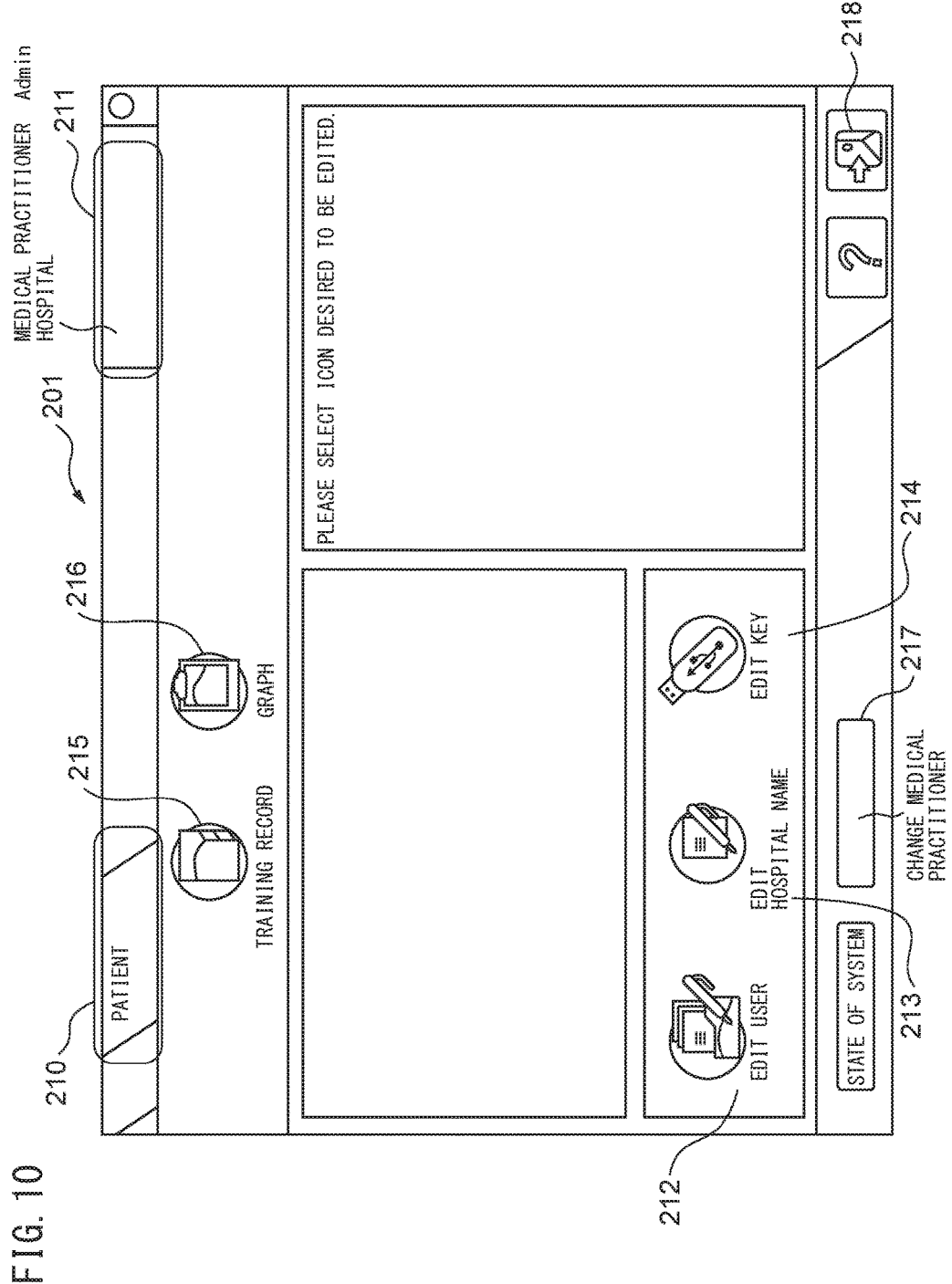
FIG. 10 is a view showing one example of a screen generated by a terminal application program.

First, the terminal application program 200 will be explained. FIG. 10 is a view showing one example of the screen generated by the terminal application program 200 and is the main menu screen 201 after log in. The screen generated by the terminal application program 200 is shown on the display 3a (FIG. 1) of the medical practitioner terminal 3.

Referring to FIG. 10, at the top left of the main menu screen 201, a patient name field 210 is arranged. In the patient name field 210, the name of the patient for which the training is trying to be set or edited is displayed. Further, at the top right of the main menu screen 201, a log in user information field 211 is arranged. In the log in user information field 211, the logged in user name, for example the name of the medical practitioner, and the hospital name are displayed. Furthermore, at the main menu screen 201, a user edit button 212, a hospital name edit button 213, a key (medical practitioner key 4 and patient key 5) edit button 214, a training record button 215, a graph button 216, medical practitioner change button 217, and a log out button 218 are arranged.

If clicking on the user edit button 212, a screen for registering the medical practitioner and registering, deleting, and editing a patient is displayed. By registering the medical practitioner, the practitioner is registered on the list of medical practitioners in the terminal application program 200. By the medical practitioner being registered on the medical practitioner list, a medical practitioner key 4 of the registered medical practitioner can be prepared. By registering a patient, the patient is registered on a patient list in the terminal application program 200. By the patient being registered on the patient list, a patient key 5 of the registered patient can be prepared. Note that, on the screen for registering, deleting, and editing a patient, not only the patient name, gender, and date of birth can be input but also the side of impairment, that is, left impairment, right impairment, or double impairment, can be selected.

If clicking on the edit button 213 of the hospital name, a screen for registering the hospital name is displayed. When the medical practitioner terminal 3 is used to first start up the terminal application program 200, the hospital name is always first registered.

If clicking on the key edit button 214, a screen for preparation and change of the medical practitioner key 4 and patient key 5 is displayed. By connecting the medical practitioner key 4 to the medical practitioner terminal 3 and preparing the medical practitioner key 4, only information of the medical practitioner selected from the registered medical practitioners is stored in the medical practitioner key 4. Further, by changing the medical practitioner key 4, only information of another medical practitioner selected from the registered medical practitioners is stored in the medical practitioner key 4 overwriting previous information. That is, the information of the medical practitioner able to be stored in the medical practitioner key 4 is a single person's worth of information. Similarly, by connecting the patient key 5 to the medical practitioner terminal 3 and preparing the patient key 5, information of a patient selected from the registered patients is stored in the patient key 5. Further, by changing the patient key 5, information on another patient selected from the registered patients is stored in the patient key 5 overwriting the previous information. That is, the information of the patient able to be stored in the patient key 5 is a single person's worth of information. Further, on the screen for preparing and changing the patient key 5, the training programs or the training content tailored to the condition of the patient, that is, the content of a session storing a plurality of the training programs, can be registered, edited, and confirmed.

The training record button 215 and graph button 216 are clicked when, as explained later, confirming the record of the training performed by the patient, that is, data on the training results analyzed by time series and training content, and confirming a graph displaying them so that they are easily understandable visually. Note that, the change button 217 of the medical practitioner is clicked on when changing the logged in medical practitioner.

The main menu screen 201 changes in operable buttons depending on the logged in user, that is, the medical practitioner or system administrator, or by whether the patient key 5 is connected to the medical practitioner terminal 3. For example, the training record button 215 and graph button 216 can be clicked on only when the patient key 5 in which the training results are stored is connected to the medical practitioner terminal 3.

Figure 11:
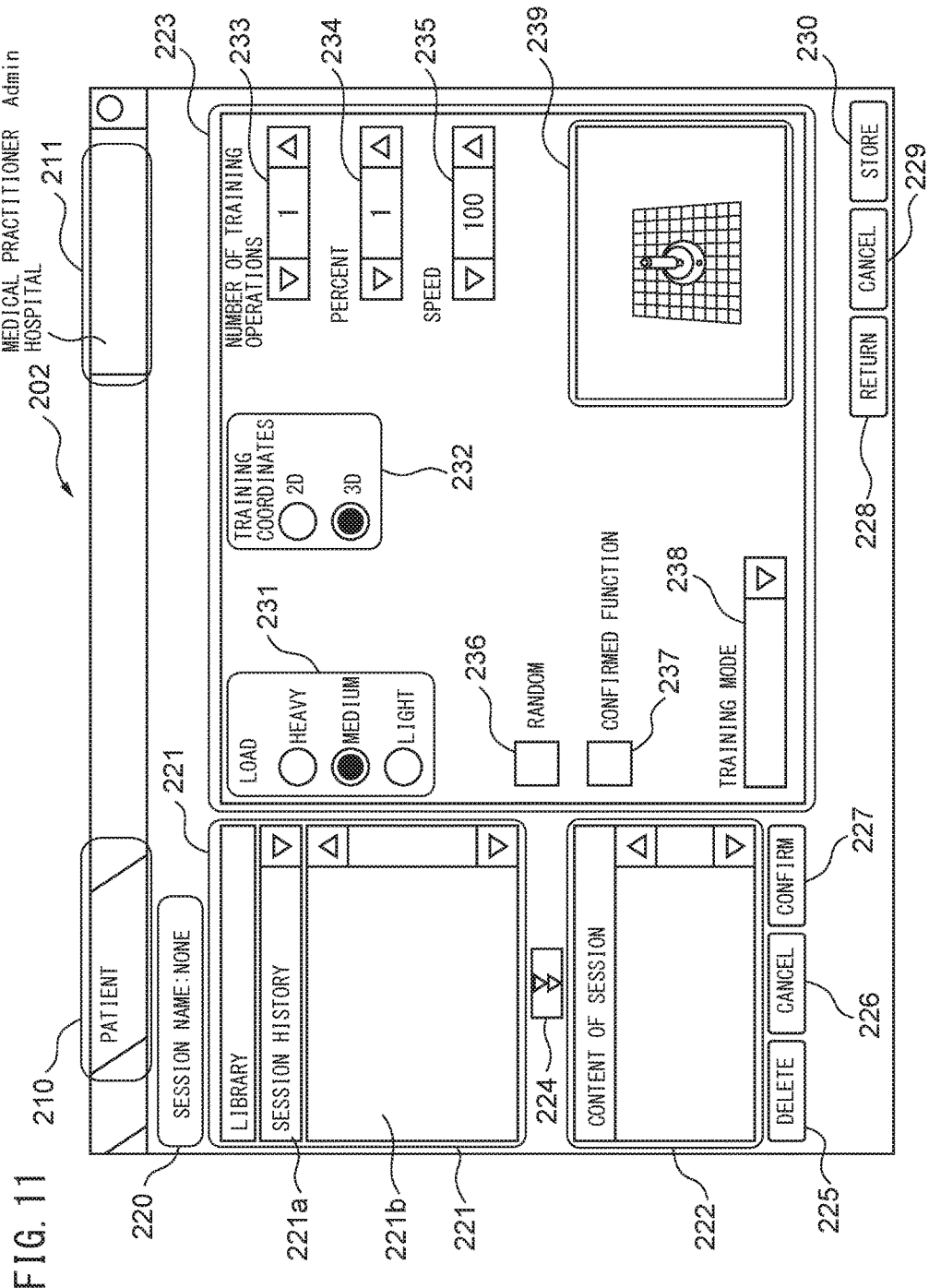
FIG. 11 is a view showing another example of a screen generated by a terminal application program.

FIG. 11 is a view showing another example of a screen generated by the terminal application program 200. It has a training content adjustment screen 202 for registering, editing, and confirming training content. The patient name field 210 and log in user information field 211 of the top left of the training content adjustment screen 202 are displayed like on the main menu screen 201. Below the patient name field 210 of the training content adjustment screen 202, a session name field 220 is arranged.

The training content adjustment screen 202 is mainly divided into two left and right regions. The left region is further divided into two top and bottom regions. In the left region of the training content adjustment screen 202, above, a library field 221 is arranged and, below, a session content field 222 is arranged. At the right region, a training content field 223 is arranged. Between the library field 221 and the session content field 222, an add button 224 is arranged. Below the session content field 222, a delete button 225, cancel button 226, and confirm button 227 are arranged. At the bottom right of the training content adjustment screen 202, a return button 228, cancel button 229, and store button 230 are arranged.

At the library field 221, a pull down menu field 221a and a training display field 221b are arranged. In accordance with the content of the menu selected from the pull down menu field 221a, the training pattern displayed at the training display field 221b changes. In the pull down menu field 221a of the library field 221, "basic training pattern", "session history", and "training history" can be selected. If selecting the basic training pattern, as explained later, a list of several basic training patterns set in advance is displayed at the training display field 221b. If selecting the session history, the history of sessions prepared in the past for the patient of the connected patient key 5 is displayed at the training display field 221b, while if selecting the training history, the history of training patterns performed in the past by the patient of the connected patient key 5 is displayed at the training display field 221b.

Here, a "session" means a combination of several training patterns of the same type or different types adjusted in accordance with the condition of the patient, that is, a training plan defining the sequence of execution of the same. It is also called "training information". The content of a session should be changed and optimized according to the change in condition of the patient, that is, usually the state of recovery. Therefore, the patient key 5 records only one session.

One session is prepared by selecting training patterns displayed in the training display field 221b of the library field 221 and clicking on the add button 224 so that they are added to the session content field 222. The training in rehabilitation successively performs the training patterns displayed at the session content field 222 from the top to the bottom. The order of the training patterns displayed at the session content field 222 can be changed by a drag and drop operation etc. of a mouse or other pointing device. Further, if clicking on the delete button 225, training patterns selected at the session content field 222 are deleted. If clinking on the cancel button 226, all of the training patterns at the session content field 222 are deleted.

At the training content field 223, the settings of the training patterns selected at the session content field 222 are displayed. At the training content field 223, the displayed training patterns are adjusted. At the training content field 223, a load field 231, training coordinate field 232, training repetition field 233, percent field 234, speed field 235, random field 236, confirmation function field 237, training mode field 238, and training diagram field 239 are arranged.

At the load field 231, the extent of the load felt when a patient moves the arm part 30 is selected from "heavy", "medium", and "light". In the training coordinate field 232, the range of movement of the arm part 30 is selected from either "2D" or "3D". The training coordinate field 232 is sometimes not displayed depending on the training patterns selected at the session content field 222. In the training repetition field 233, the number of times a training pattern is repeated is changed in accordance with the condition of the patient. In the percent field 234, the numerical value is changed so as to enlarge or reduce the operating range in accordance with the condition of the patent based on the operating range determined in advance on the program as the initial value. In the speed field 235, the speed of movement of the arm part 30 in the training pattern is changed in accordance with the condition of the patient. In the random field 236, the order of target points to be reached at the holding part 20 is randomly set. The confirmation function field 237 is set so that when the holding part 20 reaches a target point, the controller 12 is operated so that the patient can engage in the training while confirming it. Due to this, it is possible to prevent the patient from engaging in training in a lazy manner and to perform more interactive training.

In the training mode field 238, as explained later, a list of a plurality of basic training modes set in advance is displayed and one can be selected among them. In the training diagram field 239, the trajectory of a selected training pattern is displayed. Finally, by clicking on the confirm button 227, the adjustment of the training content is ended. Further, at the patient key 5, the content of the session is recorded together with the information of the patient.

Next, the basic training patterns will be explained. The basic training patterns include the 17 patterns of "8-direction suspension", "8-direction reach (counterclockwise)", "8-direction reach (clockwise)", "zigzag trajectory", "circular trajectory", "polygonal trajectory 1", "polygonal trajectory 2", "forward reach", "circumduction reach", "abductive reach (2D)", "radial reach (2D)", "radial reach (3D)", "radial reach (elevation)", "radial reach (depression)", "simulated reach (mouth)", "simulated reach (shoulder)", and "simulated reach (head)". However, other training patterns may also be included as basic training patterns.

FIG. 12 to FIG. 26 are training diagrams of the basic training patterns displayed at the training diagram field 239. At each training diagram, the direction, position, angle, order, etc. in, to, and by which the arm part 30 should be made to move from the start point of the arm part 30 are shown as target points. In other words, the motions of training which a patient should engage in are shown by showing the motions of the arm part 30. The circle marks indicate the target points. When there are a plurality of target points, the arm part 30 is made to move to them in the order of the numerals attached to the sides of the circle marks. The Point A is the basic position, that is, the initial position. The line connecting a target point and basic position shows the route which should be followed. Note that, if placing a check mark in the above-mentioned random field 236, the order of the numerals is made random.

Figure 12:
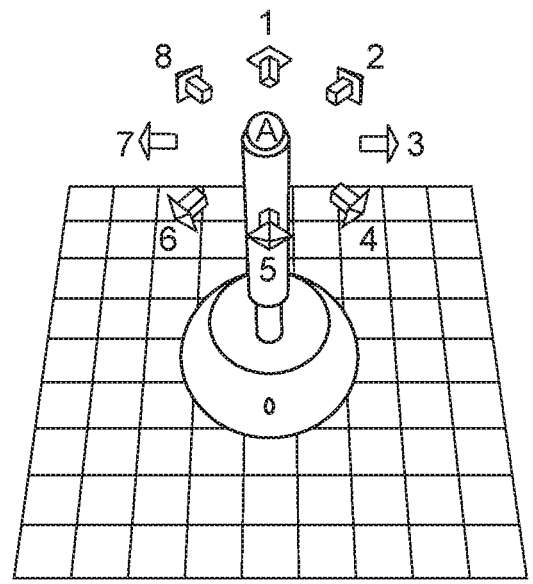
FIG. 12 is a training diagram for 8-direction suspension.

FIG. 12 is a training diagram of 8-direction suspension. The training of 8-direction suspension is comprised of a center point and 8-direction target points. The patient starts training from the height of his or her chest so that the shoulder joint abduction is 70 degrees and elbow flexion is 90 degrees and applies force toward a target point. When the target point is reached, the target point changes color from red to yellow. The patient holds the arm part 30 for several seconds so as to maintain the yellow state.

Figure 13:
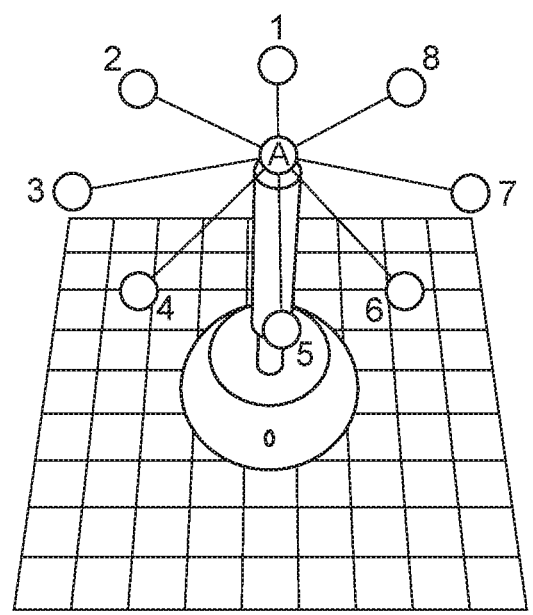
FIG. 13 is a training diagram for 8-direction reach (counterclockwise).
Figure 14:
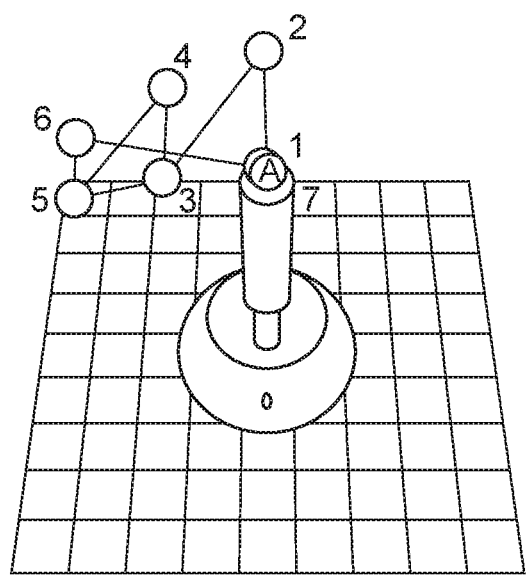
FIG. 14 is a training diagram for a zigzag trajectory.
Figure 15:
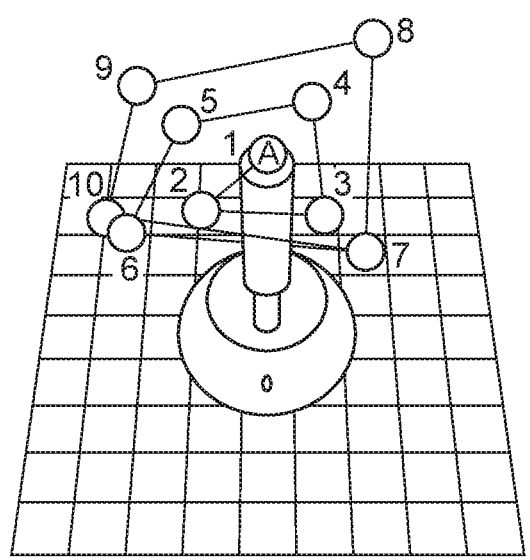
FIG. 15 is a training diagram for a circular trajectory.
Figure 16:
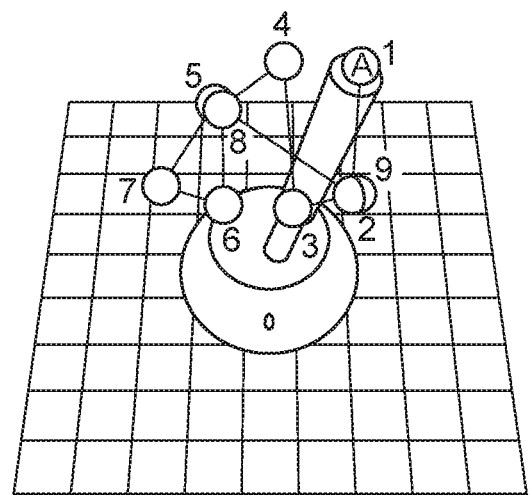
FIG. 16 is a training diagram for a polygonal trajectory 1.
Figure 17:
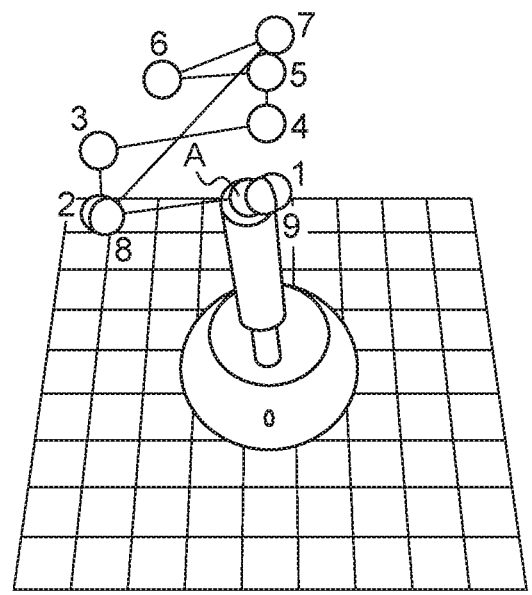
FIG. 17 is a training diagram for a polygonal trajectory 2.

FIG. 13 is a training diagram of 8-direction reach (counterclockwise), FIG. 14 is a training diagram of a zigzag trajectory, FIG. 15 is a training diagram of a circular trajectory, FIG. 16 is a training diagram of a polygonal trajectory 1, and FIG. 17 is a training diagram of a polygonal trajectory 2. The training of 8-direction reach (clockwise) performs an operation in the reverse order to the numerals shown in FIG. 13. The patient starts the training from a limb position of a shoulder joint abduction of 70 degrees and elbow flexion of 90 degrees.

Figure 18:
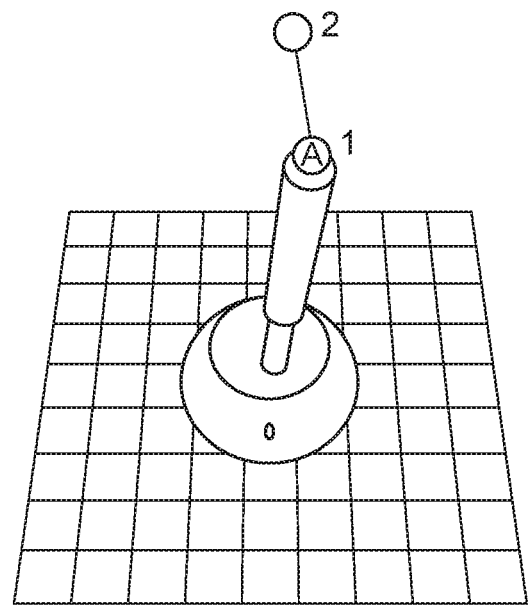
FIG. 18 is a training diagram for forward reach.
Figure 19:
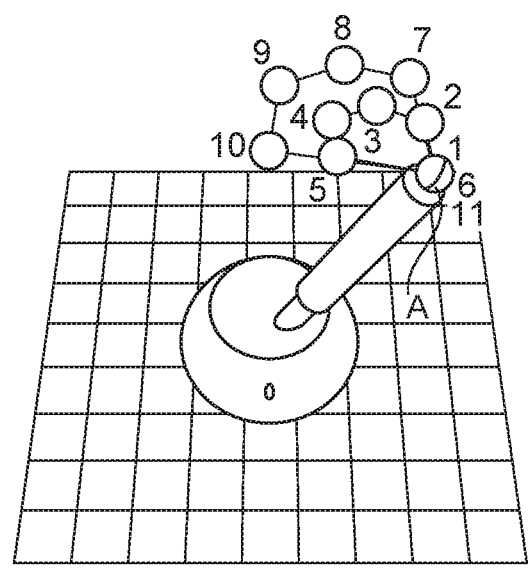
FIG. 19 is a training diagram for circumduction reach.
Figure 20:
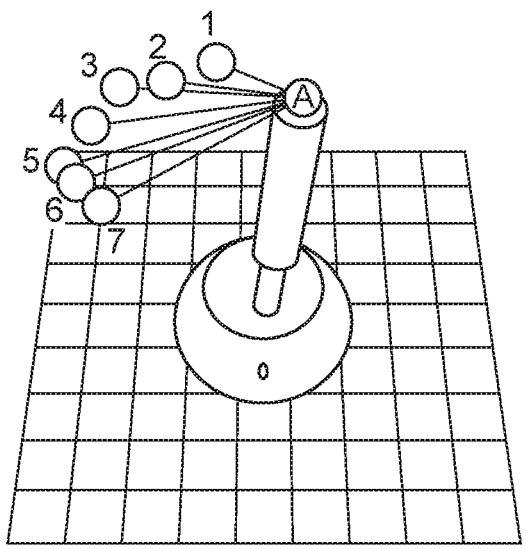
FIG. 20 is a training diagram for abduction reach (2D).

FIG. 18 is a training diagram of forward reach. When engaging in this training, the patient starts the training from a limb position of a shoulder joint abduction of 80 degrees to 90 degrees and elbow flexion of 90° and pushes the arm part 30 forward. FIG. 19 is a training diagram of circumduction reach. The patient starts the training from a limb position of a shoulder joint abduction of 0 degree and elbow flexion of 90 degrees and swings the arm part 30 to the front outward direction. FIG. 20 is a training diagram of abduction reach (2D). The patient starts the training from a limb position of a shoulder joint abduction of 80 degrees to 90 degrees and elbow flexion of 90 degrees and moves the arm part 30 not only to the front, but also radially outward.

Figure 21:
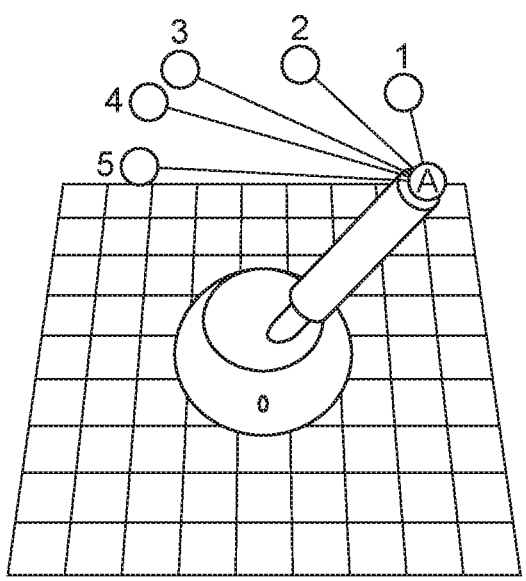
FIG. 21 is a training diagram for radial reach (2D).
Figure 22:
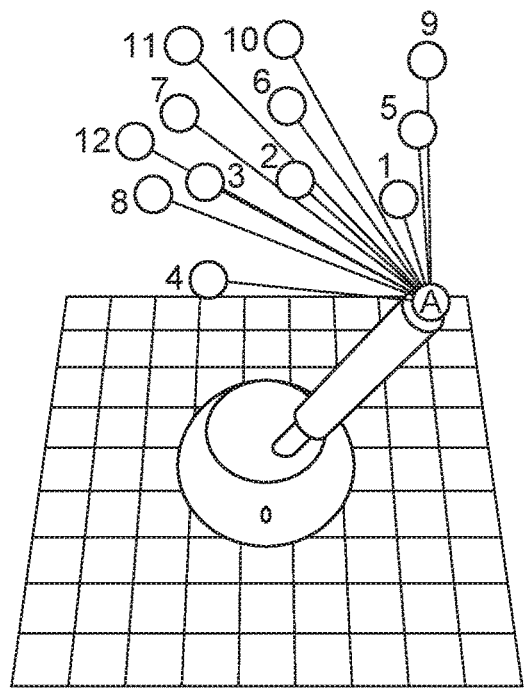
FIG. 22 is a training diagram for radial reach (3D).
Figure 23:
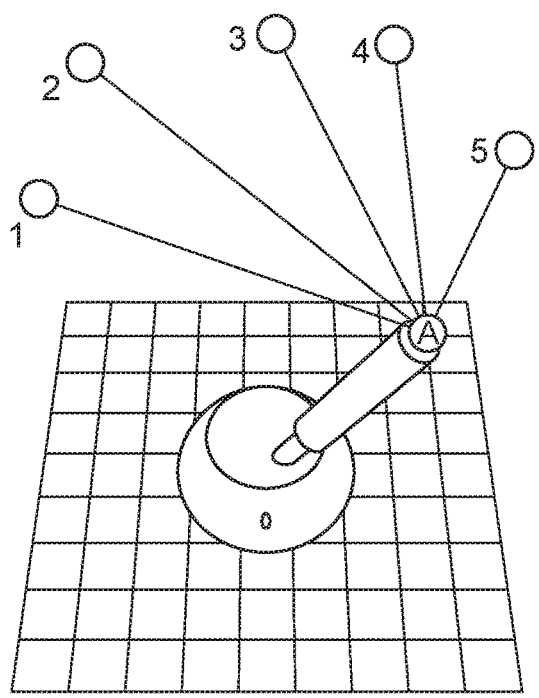
FIG. 23 is a training diagram for radial reach (elevation).
Figure 24:
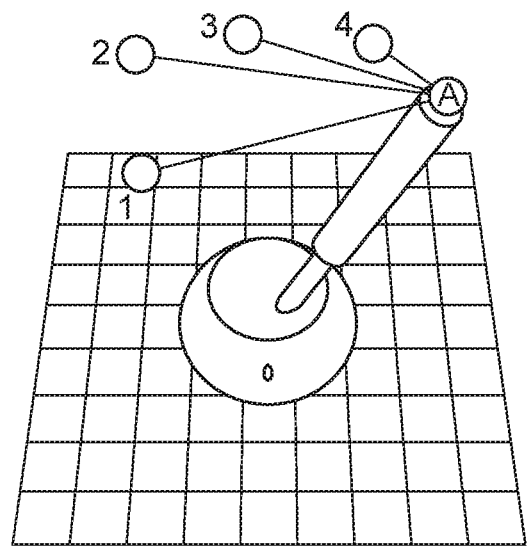
FIG. 24 is a training diagram for radial reach (depression).

FIG. 21 is a training diagram of radial reach (2D). The patient starts the training from a limb position of a shoulder joint abduction of 0 degree and elbow flexion of 90 degrees and pushes the arm part 30 radially forward. FIG. 22 is a training diagram of radial reach (3D). The patient starts the training from a limb position of a shoulder joint abduction of 0 degree and elbow flexion of 90 degrees and moves the arm part 30 upward in three dimensions. FIG. 23 is a training diagram of radial reach (elevation). The patient starts the training from a limb position of a shoulder joint abduction of 0 degree and elbow flexion of 90 degrees and pushes out the arm part 30 three-dimensionally in the upward direction radially forward. FIG. 24 is a training diagram of radial reach (depression). The patient starts the training from a limb position of a shoulder joint abduction of 0 degree and elbow flexion of 90 degrees and pushes out the arm part 30 three-dimensionally in the downward direction radially forward.

Figure 25:
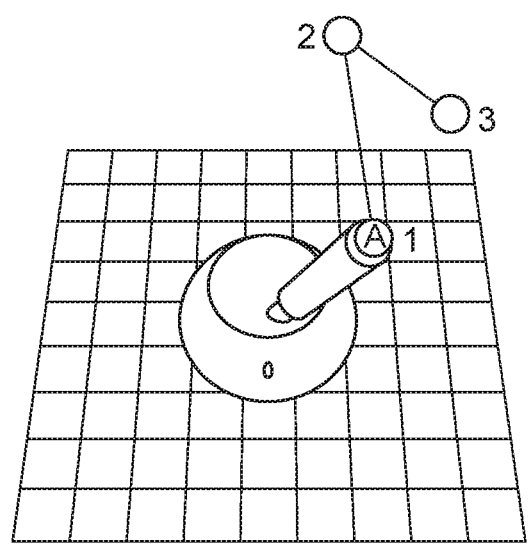
FIG. 25 is a training diagram for simulated reach (mouth).
Figure 26:
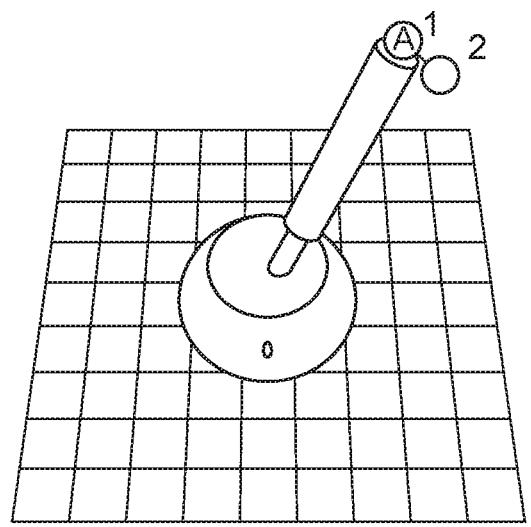
FIG. 26 is a training diagram for simulated reach (shoulder).
Figure 27:
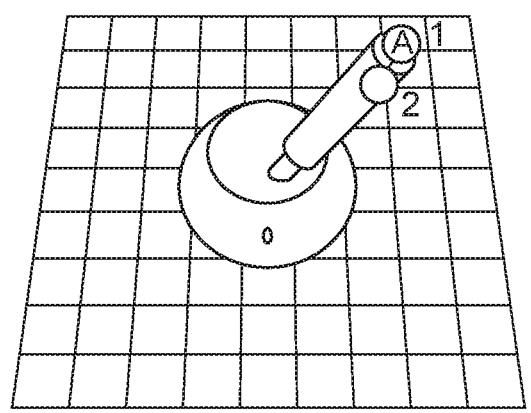
FIG. 27 is a training diagram for simulated reach (head).

FIG. 25 is a training diagram of simulated reach (mouth). In this training, in training motion for carrying a cup placed on a table to the mouth, it is possible to train motion simulating part of daily life. FIG. 26 is a training diagram of simulated reach (shoulder). In this training, it is possible to train the motion of lifting up an upper extremity while making the scapula turn inward from the limb position of a shoulder joint abduction of 0 degree and elbow flexion of 45 degrees until the elbow completely flexes. FIG. 27 is a training diagram of simulated reach (head). In this training, it is possible to train motion for raising an upper extremity from the waist position toward the head.

Next, the training modes will be explained. The training modes include five modes differing according to how the training operation of the patient is supported by the rehabilitation support apparatus 1, that is, "Guided mode", "Initiated mode", "Step initiated mode", "Follow assist mode", and "Free mode". The training modes become more advanced training modes in the order described. The training mode can be selected in accordance with the condition. That is, if the condition is severe, an easier training mode is selected, while if the condition is mild, a more advanced training mode is selected. However, other training modes may also be included.

In the Guided mode, the arm part 30 automatically operates along the trajectory of the training patterns of the session. That is, in the Guided mode, the patient is not made to actively move. The arm part 30 operates passively by the rehabilitation support apparatus 1. The Guided mode corresponds to training similar to manipulative therapy which promotes voluntary motion by assistance.

In the Initiated mode, the patient applies force in the correct direction corresponding to the training patterns of the session at the time of initial movement of the arm part 30 whereby the arm part 30 automatically moves along the trajectory of the training patterns. Therefore, the Initiated mode promotes voluntary motion by a patient without the muscular strength to reach the target point and assists reaching the target point.

In the Step initiated mode, the trajectory of the training patterns in a session is divided into a plurality of segments. The patient applies force in the correct direction at the time of initial movement of the arm part 30 in each segment whereby the arm part 30 automatically moves along the trajectory of the training patterns. If the patient does not apply force in the correct direction at the end point of each segment, that is, at the start point of the next segment, the arm part 30 stops. Therefore, the patient has to intermittently move his or her upper extremity voluntarily. This is a higher training mode than the Initiated mode.

In the Follow assist mode, the arm part 30 automatically moves along the trajectory of the training patterns of the session. The patient voluntarily applies force in accordance with this operation. At that time, if the patient applies force in the correct direction along the trajectory, the arm part 30 accelerates. If applying force in a direction away from the trajectory, the arm part 30 decelerates. In the Follow assist mode, it is possible to learn voluntary motion in only a certain direction.

In the Free mode, the arm part 30 will not automatically move. Further, no assistance is provided for causing motion along the trajectory of the training patterns. If the patient applies force to the arm part 30, the speed and acceleration change in accordance with the strength of the force applied and the arm part 30 moves in the direction in which the patient applies force. The patient can freely move the holding part 20 within the range of movement of the arm part 30. In the Free mode, it is possible to learn coordinated movement of the muscles moving in response to movement of the upper extremity.

Figure 28:
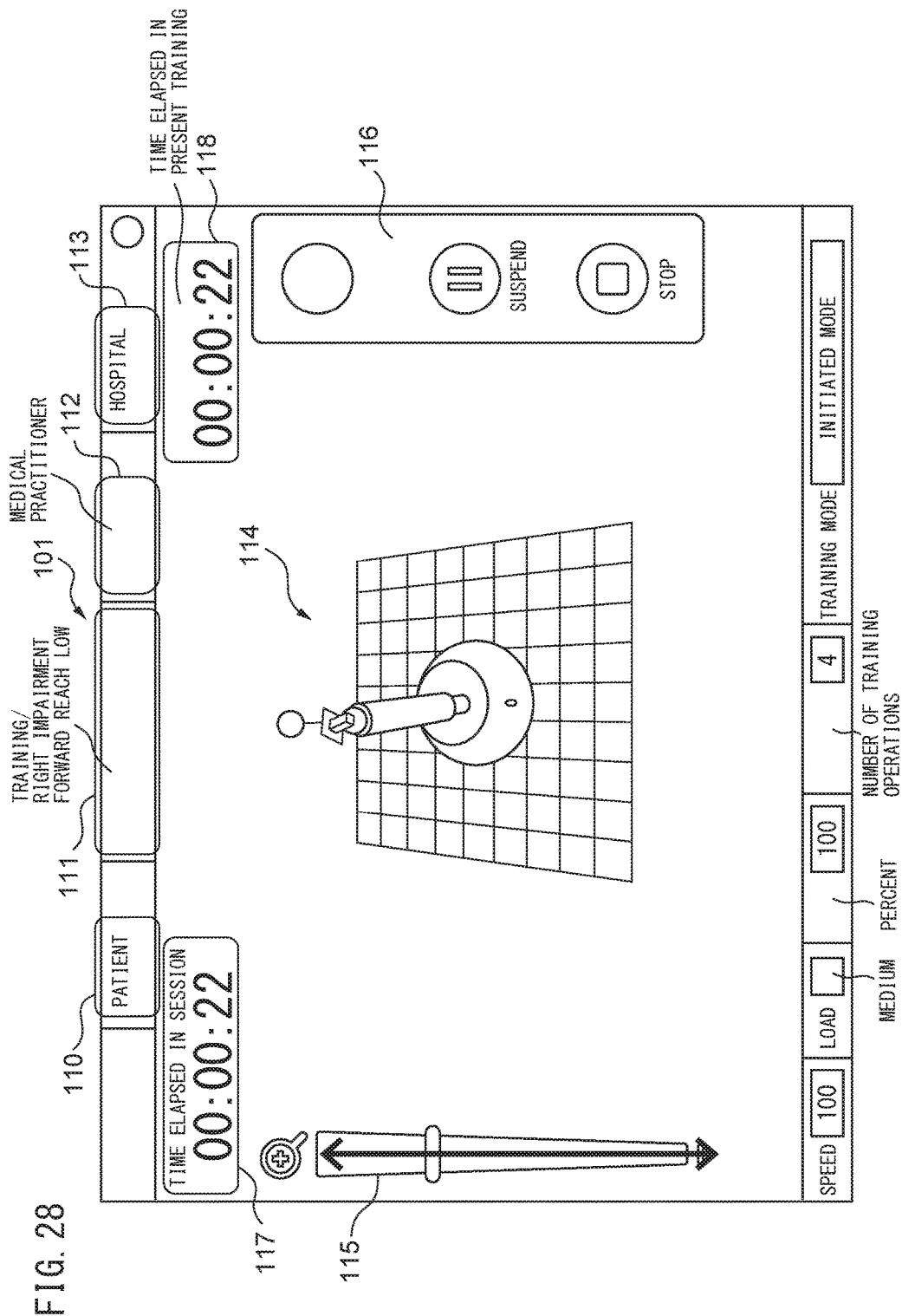
FIG. 28 is a view showing one example of a screen generated by an apparatus application program.

Next, the apparatus application program 100 will be explained. FIG. 28 is a view showing one example of the screen generated by the apparatus application program 100. This is the training screen 101 after finishing all of the initialization before training. The screen generated by the apparatus application program 100 is shown on the display 40.

Referring to FIG. 28, on the display bar at the top part of the training screen 101, the patient name field 110, current training pattern field 111, medical practitioner name field 112, and hospital name field 113 are arranged. At the display bar at the bottom part of the training screen 101, the set content of the training patterns displayed in the training pattern field 111 is displayed. The training pattern field 111 successively displays training patterns in accordance with the content of the session prepared in advance. At the center of the training screen 101, a training diagram field 114 at which the state of the arm part 30 is displayed in real time is arranged. At the left of the training diagram field 114, a size bar 115 serving as the reference for enlarging or reducing the training diagram field 114 by operation of the controller 12 is arranged. Further, at the right of the training diagram field 114, an operation display part 116 showing images of buttons arranged at the controller 12 corresponding to commands sent to the rehabilitation support apparatus 1 at the time of "start", "suspend", "stop", and other operations in training by operation of the controller 12 is arranged. Furthermore, at the training screen 101, a session elapsed time field 117 showing the elapsed time of a session and a training pattern elapsed time field 118 showing the elapsed time of a training pattern are arranged.

The training diagram field 114 shows the direction, position, angle, sequence, etc. in, to, and by which the arm part 30 should be made to move from the basic position A of the arm part 30 together with the real time state of the arm part 30 in accordance with the training patterns such as shown in for example FIG. 12 to FIG. 27. Further, the direction of force applied to the arm part 30 calculated based on signals detected by various types of sensors is shown by arrows.

When a medical practitioner key 4 is connected to the rehabilitation support apparatus 1, it is possible to change the content of the session prepared at the medical practitioner terminal 3. That is, the apparatus application program 100 has screens and functions corresponding to the training content adjustment screen 202 of the terminal application program 200. For this reason, the apparatus application program 100 and terminal application program 200 may be substantially the same programs.

When first using the rehabilitation support apparatus 1, first, the medical practitioner key 4 is connected to the rehabilitation support apparatus 1 to load the hospital name stored in the medical practitioner key 4 into the storage part 80 of the rehabilitation support apparatus 1. Next, the patient key 5 is connected to the rehabilitation support apparatus 1 to load the information of the patient and content of the session stored in the patient key 5 into the storage part 80 of the rehabilitation support apparatus 1. Note that, the connected medical practitioner key 4 and patient key 5 may also be deemed part of the storage part 80 of the rehabilitation support apparatus 1.

For example, a patient training his or her right arm sits in the chair 2 and fastens his or her right arm to the holding part 20 of the arm part 30. The holding part 20 is adjusted by changing the seat height of the chair 2 so as to become the optimal height corresponding to the height of the patient engaged in the training. Next, to enable the patient to safely engage in effective training, the apparatus application program 100 is used to load the range of motion of the patient into the storage part 80 of the rehabilitation support apparatus 1 and the patient key 5 connected to the rehabilitation support apparatus 1. In this case, both the range of compulsory motion using the Guided mode and the range of autonomous motion using the Free mode are stored.

Figure 29:
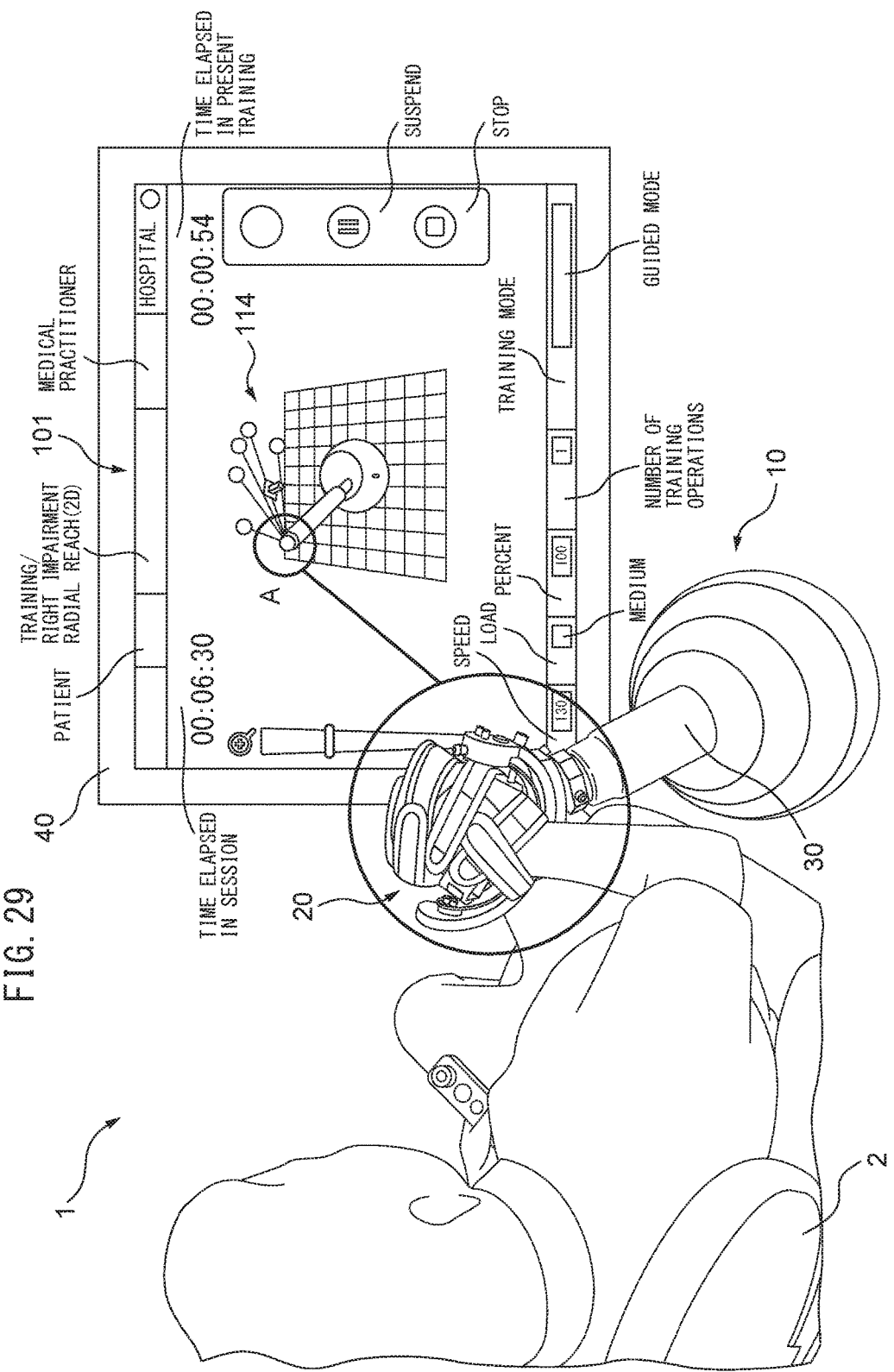
FIG. 29 is a view showing the state of a patient engaged in training.

FIG. 29 is a view showing the state of a patient engaged in training. The patient engages in training while viewing the training screen 101 shown on the display 40, in particular the training diagram field 114. The history of the session and training patterns for the training is stored in the storage part 80 of the rehabilitation support apparatus 1 and the patient key 5 connected to the rehabilitation support apparatus 1. Further, various training logs are similarly stored in the storage part 80 and patient key 5 based on the positions, angles, forces and pressures, times, etc. detected by various types of sensors.

The training log includes, for example, the speed and acceleration of the holding part 20, the movable range of the joint, the distance moved at the time of training, the difference in the distance from the ideal trajectory, the training time (time until reaching route), the load vector in the space, etc. Here, the training log plus the content of the session corresponding to it, that is, information including the training mode and training patterns and the first registered age, gender, etc. are referred to as the "motion information". That is, after the end of training, the storage part 80 and patient key 5 store motion information including the training log together with the content of the session stored before the start of the training.

Next, the motion assessing part 72 assessing the training based on the content of the session of the training performed and its results will be explained. That is, the motion assessing part 72 generates assessment information based on the training information and motion information.

The motion assessing part 72, for example, generates motion information, in particular, information calculated from the training log such as the "ratio of resistance", "ratio of voluntary motion", "movable range of assisted motion", "time from start point to target point", "movable range of unassisted motion", "accuracy of direction of force", "accuracy of motion trajectory", "smoothness of motion", and other such assessment information. If clicking on the training record button 215 and graph button 216, such assessment information is displayed in two ways as a training record and graphs and can be printed out. Further, the graph data can be output to a file.

The "ratio of resistance" shows the ratio of the time when force was not applied in the correct direction during training. If the motor function is improved, it becomes close to 0%.

The "ratio of voluntary motion" shows the ratio of the range of motion in the Guided mode and the range of motion in the Free mode. If the motor function is improved, it becomes close to 100%.

The "movable range of assisted motion" shows the ratio of the straight line distance from the start point to the target point and the range of motion by assisted motion (distance). Here, "assisted motion" means all training modes other than the Free mode. If the motor function is improved, it becomes close to 100%.

The "time from start point to target point" shows the time from the start point until reaching the target point. It is the average value of the times from all start points to the target points. If the motor function is improved, it becomes close to 0.

The "movable range of unassisted motion" shows the ratio of the distance set at training and the distance of the trajectory followed in training. If the motor function is improved, it becomes close to 100%.

The "accuracy of direction of force" shows the ratio of the time during which correct force is applied in the direction of the target point. If the motor function is improved, it becomes close to 100%.

The "accuracy of motion trajectory" shows the ratio of the straight line distance from the start point to the target point and the distance of the actually followed trajectory. If the motor function is improved, it becomes close to 100%.

The "smoothness of motion" shows the ratio of the number of peaks of speed from the start point to the target point and the actual number of peaks. The ideal number of peaks of speed is 1. If the motor function is improved, it becomes close to 100%.

When displaying the assessment information by graphs, the types of the graphs displayed change in accordance with the displayed training mode due to the difference in features of the training modes. In the results of the Guided mode, graphs of the ratio of resistance, ratio of voluntary motion, and movable range of assisted motion are displayed. In the results of the Initiated mode, graphs of the ratio of resistance, time from start point to target point, and movable range of assisted motion are displayed. In the results of the Step initiated mode, the time from start point to target point and movable range of unassisted motion are displayed. In the results of the Follow assist mode, a graph of the accuracy of direction of force is displayed. In the Free mode, graphs of the accuracy of the exercise trajectory, smoothness of motion, accuracy of direction of force, and movable range of unassisted motion are displayed.

Note that, the assessment information may include not only motion information, but also information calculated from the training log together with other information as assessment information. In addition to the calculated quantitative data, it may also be a visual graphic showing the ideal trajectory and actual trajectory.

Next, the training information setting part 73 generating the optimum session for the patient will be explained. The training information setting part 73 generates new training information based on the content of the session, that is, the training information and the assessment information of training by that content.

As the basic thinking in training in rehabilitation, even if a patient repeats motion which can be easily performed, there is little effect and, further, motion greatly exceeding the limits of the patient would rather obstruct recovery. Motion slightly exceeding the limits of the patient in movable range of the joints, load, etc. is important.

Therefore, the training information setting part 73 analyzes the assessment information of different items such as the ratio of resistance and accuracy of direction of force. The training information setting part 73 generates new training information and updates the current training information so as to raise the level of training (that is, the difficulty) when these items are predetermined assessments or more and lower the level of training when they are predetermined assessments or less. The training information setting part 73 does not generate new training information but uses the previous training information at the time of the next training when as a result of analysis the training information is neither a predetermined assessment or more or less.

Further, the training information setting part 73 may raise or lower the level of training considering the physical condition at the time of training and other temporary factors if a predetermined assessment continues for a predetermined number of times. For example, the ratio of free motion, as explained above, approaches 100% if the motor function is improved, so if 90% continues three times successively, the level of training may be raised, while if 60% continues three times successively, the level of training may be lowered.

The level of training may be adjusted by changing the above-mentioned training mode and training patterns, by adjusting other items included in the training content adjustment screen 202, for example, the load field 231 or percent field 234 etc., or by finer adjustment. For example, first, training is performed by the Guided mode, but this may be switched to the Initiated mode so as to raise the level of training. Further, even in the case of a series of training patterns, for example, the radial reach (2D) such as shown in FIG. 21, it is possible to decrease the number of training operations in the direction which the patient is good at, for example, the direction toward the target point 1, and increase the number of training operations in the direction which the patient is bad at, for example, the direction toward the target point 5. Similarly, in the load field 231 of the training content adjustment screen 202, it is also possible to raise the load in the direction which the patient is good at and lighten the load in the direction which the patient is bad at. Further, at the percent field 234 of the training content adjustment screen 202, the operating range can be expanded or contracted.

When generating new training information, the training information setting part 73 may also select it from predetermined standard sessions. A standard session, for example, is based on a session which starts with "reflex" and successively includes "conjugate movement", "disjunctive movement", and "individual articular movement", that is, a session performed by more severe patients.

In the reflex session, the training pattern is selected from suitable training patterns for the condition of the patient, while the training mode is the Guided mode. In the conjugate movement session, the training pattern can be selected from suitable training patterns for the condition of the patient, while the training mode is either the Guided mode or the Initiated mode. In the disjunctive movement session, the training pattern can be selected from forward reach, abduction reach (2D), radial reach (2D), and circumduction reach, while the training mode can be selected from the Guided mode, Initiated mode, Step initiated mode, and Follow assist mode. In the individual articular movement session, the training pattern can be selected from forward reach, abduction reach (2D), radial reach (2D), circumduction reach, and radial reach (3D), while the training mode can be selected from the Guided mode, Initiated mode, Step initiated mode, Follow assist mode, and Free mode.

The training information setting part 73 may further generate separate new training information based on the assessment information of training by one session and assessment information of training by a new session generated as a result. That is, it is possible to engage in training based on the new training information generated by the training information setting part 73 and check the assessment information for the same so as to assess the generated training information. In other words, it is possible to use the training information which the training information setting part 73 generated as feedback and apply it to the generation of the next training information. The training information setting part 73 can use the results of motion information of the patient based on the generated training information as feedback to generate more efficient and effective training information.

At the time of generation of training information by the training information setting part 73 or at the time of feedback of the generated training information, it is also possible to refer to and utilize the assessment information and training information of other patients stored in the storage part 80 of the rehabilitation support apparatus 1. That is, if there are assessment information and training information of patients with conditions even partially similar, it becomes possible to generate efficient and effective training information based on the same. Such assessment information and training information may be shared with other rehabilitation support apparatuses 1 through USB memories and other portable storage devices.

For example, the motion information, assessment information, and training information of one severe case patient are accumulated over the long period until recovery. Similarly, these information are similarly accumulated for a plurality of patients such as patients with the same extents of conditions and patients differing in location of impairment. Based on the accumulated information, a training result database is constructed. The training result database is stored in the storage part 80 of the rehabilitation support apparatus 1 or the storage part of the medical practitioner terminal 3. The training information setting part 73 may refer to the training result database for matching processing to thereby extract assessment information and training information similar to that patient and generate new training information.

Next, the assessment information predicting part 74 generating future predicted assessment information, that is, predicted assessment information, based on the assessment information of a patient at the present point of time will be explained. The assessment information predicting part 74 refers to the trends in assessment information of other patients stored in the storage part 80 of the rehabilitation support apparatus 1 or recovery curves of patients stored in advance as general information in the storage part 80 of the rehabilitation support apparatus 1 etc., that is, changes along with time, while generating future predicted assessment information based on the assessment information of the patient at the current point of time.

For example, at the time of prediction by the assessment information predicting part 74, the above-mentioned training result database may also be utilized. The assessment information predicting part 74 may refer to the training result database for matching processing to thereby extract assessment information and training information similar to that patient and generate predicted assessment information. By providing the patient with predicted assessment information, it is possible to maintain the motivation of the patient with respect to the training.

Figure 30:
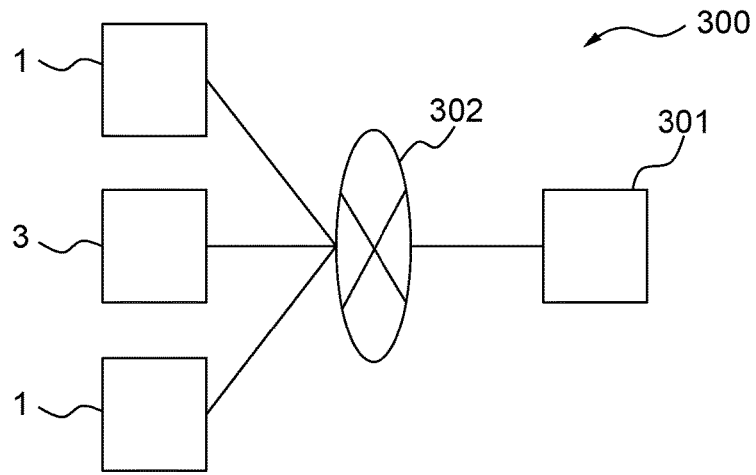
FIG. 30 is a view showing one example of the general configuration of a communication system.

FIG. 30 is a view showing one example of the general configuration of a communication system 300. The communication system 300 has a rehabilitation support apparatus 1 and medical practitioner terminal 3 having motion information, assessment information, and training information and an administrator server 301. The rehabilitation support apparatus 1 and medical practitioner terminal 3 are connected through the Internet 302. In FIG. 30, two rehabilitation support apparatuses 1 and one medical practitioner terminal 3 are connected to the Internet 302, but this is for convenience of illustration. The numbers of the rehabilitation support apparatuses 1 and medical practitioner terminals 3 connected by the Internet 302 are not limited to these. The administrator server 301 may have the above-mentioned training result database. That is, the rehabilitation support apparatus 1 and medical practitioner terminal 3 connected through the Internet 302 send motion information, assessment information, and training information to the administrator server 301, construct a training result database in the administrator server 301, and share the same. Due to this, it becomes possible to collect more information.

The training information setting part 73 or assessment information predicting part 74 of the rehabilitation support apparatus 1 or medical practitioner terminal 3 can refer to and utilize the training result database of the administrator server 301. Due to this, it becomes possible to generate training information more suitable for the patient and becomes possible to more accurately predict assessment information. Note that, the administrator server 301 may have the training information setting part 73 or assessment information predicting part 74, while the rehabilitation support apparatus 1 or medical practitioner terminal 3 may refer to the results in the administrator server 301.

Next, the assessment information converting part 75 which confirms the effects of training by the rehabilitation support apparatus 1 while converting assessment information of the rehabilitation support apparatus 1 to corresponding other assessment information or performing the reverse conversion will be explained.

There are various techniques for the method of assessing the condition and degree of recovery of a patient, that is, the method for assessing the motion functions, but in the Present Description, the Fugl-Meyer Assessment (below, "FMA") will be used. Only naturally, the present invention can also be applied to other methods of assessment.

The FMA system has 33 assessed items. The results of assessment are converted to numerical values as motor impairment scores. In the FMA, 0 point, 1 point, or 2 points is selected for each assessed item. The maximum score is therefore 66 points. As an example of the assessed items, flexion joint motion is motion of lifting the hand up to the ear at the impaired side in a sitting position. According to this motion, the flexion of the elbow, circumduction of the forearm, extension and elevation of scapula, and abduction and external rotation of the shoulder joint are assessed. As another example, extension joint motion is motion of touching the knee at the unimpaired side in a sitting position. According this motion, the adduction and internal rotation of the shoulder joint, the extension of the elbow, and the pronation of the forearm are assessed.

First, a clinical test performed using the rehabilitation support apparatus 1 will be explained. The clinical test is performed not by giving a plurality of medical practitioners an explanation relating to the preparation of the optimal session, but by getting each medical practitioner to prepare a session for a patient with impairment of the upper extremity for which he or she is in charge. The patient concerned is assessed for motor functions by FMA before starting the clinical test. After that, the patient is made to engage in training using the rehabilitation support apparatus 1 based on the sessions prepared by medical practitioners on their own judgment. The training period was 6 weeks. The medical practitioners suitably prepared new sessions tailored to the condition of the patient, while the patient engaged in training based on such new sessions. After the end of the training period, the patient was again assessed for motor functions by FMA.

Figure 31:
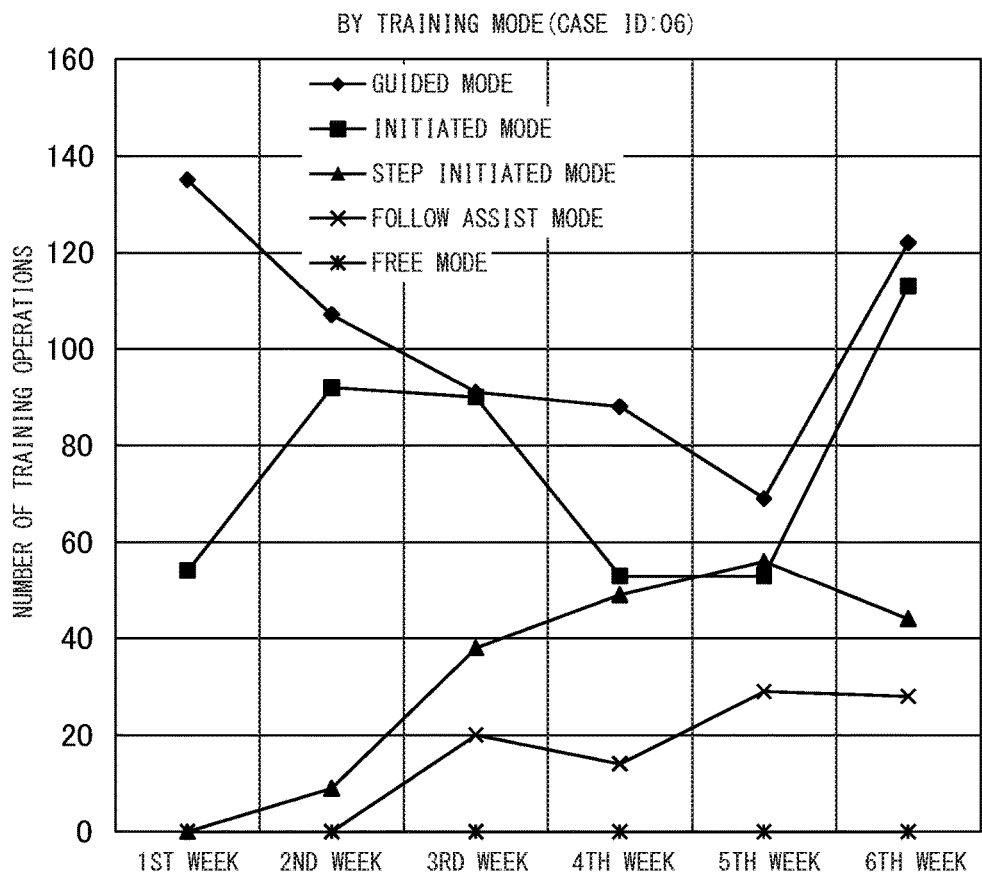
FIG. 31 is a graph of an embodiment totaling up the number of training operations for each training mode for each week for a specific patient.

FIG. 31 is a graph of examples summarizing the number of training operations for each training mode for a specific patient. In the graph of FIG. 31, the abscissa shows the weeks from the start of training, while the ordinate shows the number of training operations. Only naturally, the number of training operations for each training mode for each week differs for each patient according to the sessions prepared by the medical practitioners. Such clinical trial data for 30 patients is further summarized in Table 1 to Table 3.

Table 1 shows the results of grouping of data on the number of training operations by the different training modes by application of cluster analysis. The patients were grouped into the A group and B group and these compared. 17 patients were classified in the A group, while 13 patients were classified in the B group. The A group is the low load group in which the two modes of the Guided mode and the Initiated mode account for about 99%, while the B group is the high load group including all modes from the Guided mode to the Free mode.

TABLE 1

| Training mode | A group (17 cases) | B group (13 cases) |
|---|---|---|
| Guided mode | 67.7 | 41.1 |
| Initiated mode | 30.9 | 36.9 |
| Step initiated mode | 1.1 | 18.1 |
| Follow assist mode | 0.1 | 3.3 |
| Free mode | 0.2 | 0.6 |
| Total | 100.0 | 100.0 |

(%)

Table 2 and Table 3 show the results of classifying the patients grouped into the A group and B group in Table 1 according to whether their motor impairment scores of the FMA are less than 30 points or are 30 points or more. A motor impairment score of 30 points is the boundary condition for classification for training using the rehabilitation support apparatus 1 and is the number of points judged as the reference points of a patient generally considered a severe case. Table 2 shows the motor impairment scores of the FMA before and after a training period during in which patients with a motor impairment score of the FMA of less than 30 points use the rehabilitation support apparatus 1. A patient with a motor impairment score of the FMA of less than 30 points is, as explained above, a relatively severe case. Table 3 shows the motor impairment scores of the FMA before and after a training period during in which patients with a motor impairment score of the FMA of 30 points or more use the rehabilitation support apparatus 1. A patient with a motor impairment score of the FMA of 30 points or more is a relatively mild case.

TABLE 2

| <30 (severe cases) | A group (12 cases) | B group (5 cases) |
|---|---|---|
| Before use of system | 14.8 | 20.0 |
| After use of system | 27.4 | 28.0 |
| Amount of change | 12.6 | 8.0 |

TABLE 3

| ≥30 (mild cases) | A group (5 cases) | B group (8 cases) |
|---|---|---|
| Before use of system | 44.8 | 46.6 |
| After use of system | 48.6 | 55.9 |
| Amount of change | 3.8 | 9.3 |

If referring to Table 2 of severe cases, there were 12 patients with severe cases classified as the A group, while there were 5 patients with severe cases classified as the B group. The amount of change of the motor impairment score of patients of the low load group of the A group is 12.6 points, while the amount of change of the motor impairment score of patients of the high load group of the B group is 8.0 points. That is, for patients with severe cases, engagement in the low load training mode such as the Guided mode resulted in better recovery.

On the other hand, if referring to Table 3 of mild cases, there were 5 patients with mild cases classified as the A group, while there were 8 patients with mild cases classified as the B group. The amount of change of the motor impairment score of patients of the low load group of the A group is 3.8 points, while the amount of change of the motor impairment score of patients of the high load group of the B group is 9.3 points. That is, for patients with mild cases, engagement in the high load training mode such as the Free mode resulted in better recovery.

Figure 32:
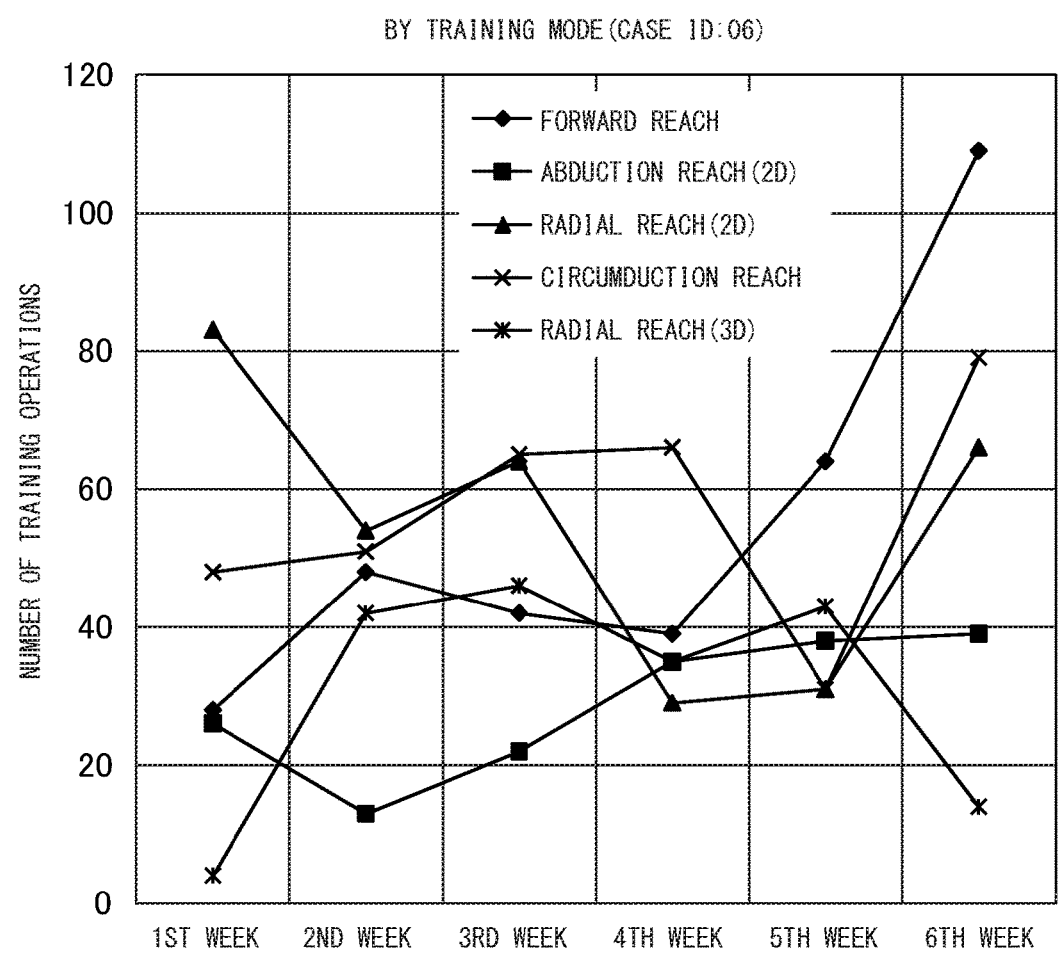
FIG. 32 is a graph of an embodiment totaling up the number of training operations for each training pattern for each week for a specific patient.

FIG. 32 is a graph of an embodiment summarizing the number of training operations for each training pattern for a specific patient. In the graph of FIG. 32, the abscissa shows the weeks from the start of training, while the ordinate shows the number of training operations. Only naturally, the number of training operations for each training pattern for each week differs for each patient according to the sessions prepared by the medical practitioners. Such clinical trial data for 30 patients is further summarized in Table 4 to Table 6.

Table 4, in the same way as Table 1, shows the results of grouping of data on the number of training operations by the different training patterns by application of cluster analysis. 10 patients were classified in the C group, while 20 patients were classified in the D group. The C group is a non-variegated group in which training is performed centered on the radial reach (2D), while the D group is a variegated group in which training is performed by five types of training patterns.

TABLE 4

| Training menu | C group (10 cases) | D group (20 cases) |
|---|---|---|
| Forward reach | 25.7 | 19.0 |
| Abduction reach (2D) | 20.0 | 9.6 |
| Radial reach (2D) | 54.2 | 39.0 |
| Circumduction reach | 0.0 | 21.7 |
| Radial reach (3D) | 0.0 | 10.8 |
| Total | 100.0 | 100.0 |

(%)

Table 5 and Table 6 show the results of classifying the patients grouped into the C group and D group in Table 4 according to whether their motor impairment scores of the FMA are less than 30 points or are 30 points or more. Table 5 shows the motor impairment scores of the FMA before and after a training period during in which patients with a motor impairment score of the FMA of less than 30 points use the rehabilitation support apparatus 1. Table 3 shows the motor impairment scores of the FMA before and after a training period during in which patients with a motor impairment score of the FMA of 30 points of more use the rehabilitation support apparatus 1.

TABLE 5

| <30 (severe cases) | C group (6 cases) | D group (11 cases) |
|---|---|---|
| Before use of system | 18.8 | 14.9 |
| After use of system | 30.7 | 25.9 |
| Amount of change | 11.9 | 11.0 |

TABLE 6

| <30 (severe cases) | C group (4 cases) | D group (9 cases) |
|---|---|---|
| Before use of system | 46.5 | 45.7 |
| After use of system | 51.3 | 53.9 |
| Amount of change | 4.8 | 8.2 |

If referring to Table 5 of the severe cases, there were six patients with severe cases classified in the C group and 11 patients with severe cases classified in the D group. The amount of change in the motor impairment score of patients of the non-variegated group of the C group was 11.9 points, while the amount of change in the motor impairment score of patients of the variegated group of the group D was 11.0 points. That is, if a patient with a severe condition, engaging in a non-variegated (simple) training pattern leads to good recovery.

On the other hand, if referring to Table 6 of the mild cases, there were four patients with mild cases classified in the C group and nine patients with mild cases classified in the D group. The amount of change in the motor impairment score of patients of the non-variegated group of the C group was 4.8 points, while the amount of change in the motor impairment score of patients of the variegated group of the group D was 8.2 points. That is, if a patient with a mild condition, engaging in a variegated training pattern leads to good recovery.

According to the above embodiments, trends in the optimal training mode and training patterns for the condition of a patient constituting a severe case or mild case became clear.

By repeating and applying such clinical tests, it becomes possible to make the scores of the individual assessment items of the FMA match with the assessment information in the rehabilitation support apparatus 1. That is, in the assessment information converting part 75 of the central processing part 70, the assessment information obtained by the FMA and the assessment information obtained by the rehabilitation support apparatus 1 can be converted to each other. Therefore, the storage part 80 stores conversion information of formulas for calculation or parameters or formats of maps for the assessment information converting part 75 to refer to.

Note that, it is also possible to enter the initial assessment information obtained by FMA through a keyboard or other interface part 62 and generate the initial session by the training information setting part 73 based on the assessment information converted by the assessment information converting part 75.

Figure 33:
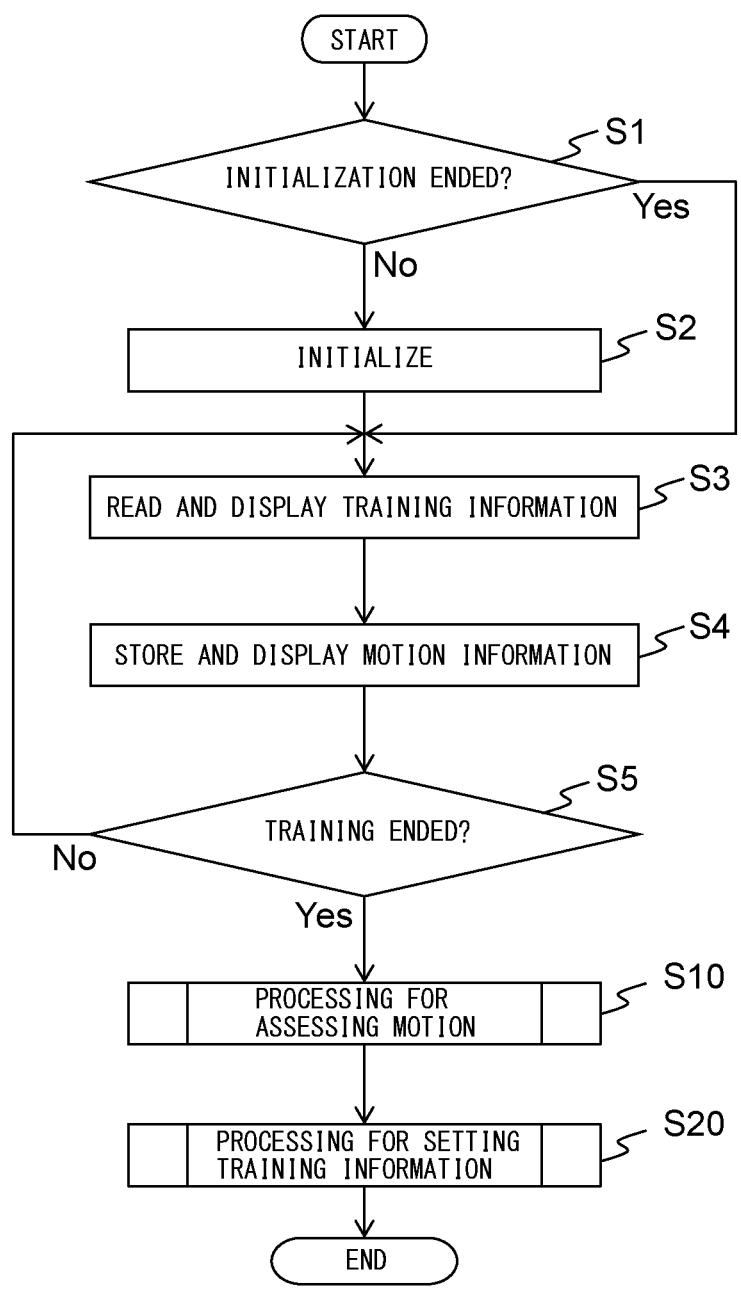
FIG. 33 is a flow chart of a method of use of a rehabilitation support apparatus according to an embodiment of the present invention.

FIG. 33 is a flow chart of the method of use of the rehabilitation support apparatus 1 according to an embodiment of the present invention.

Referring to FIG. 33, first, at step S1, before starting the training, it is judged if the initialization process has finished. If the initialization process has finished, the routine proceeds to step S3. On the other hand, if the initialization process has not finished, the routine proceeds to step S2 where the initialization is performed. The initialization consists of storage of the hospital name and the range of motion of the patient etc. in the rehabilitation support apparatus 1.

Next, at step S3, training information is read in from the storage part 80 and the read training information is shown on the display 40. The patient engages in training based on the displayed training information. Next, at step S4, motion information of the holding part 20 of the arm part 30 moved by the patient based on the displayed training information is stored in the storage part 80 and motion information is shown on the display 40 in real time. Therefore, a graphic drawing the ideal trajectory and the actual trajectory is visually fed back to the patient as assessment information of the training.

Next, at step S5, it is judged if the training has all ended. If the training has not all ended, the routine proceeds to step S3 where training is again performed. If the training has all ended, the routine proceeds to step S10. At step S10, the processing for assessing motion is performed. Next, at step S20, processing for setting the training information is performed and the processing is ended.

Figure 34:
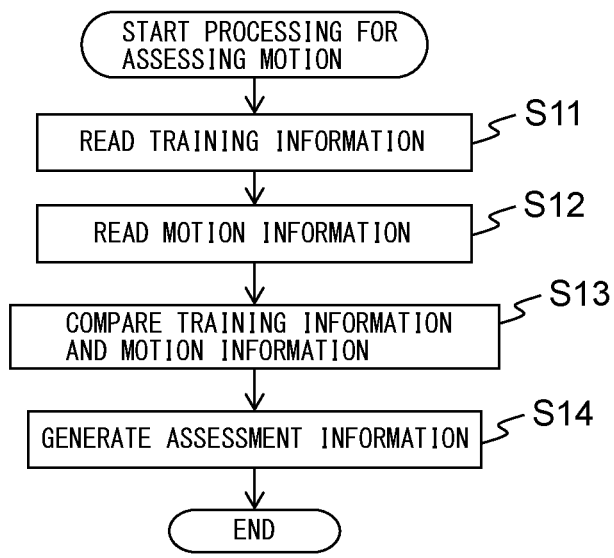
FIG. 34 is a flow chart of processing for assessing motion.

FIG. 34 is a flow chart of processing for assessing motion. The processing for assessing motion is performed by a motion assessing part 72 of the central processing part 70.

Referring to FIG. 34, first, at step S11, the training information is read in. Next, at step S12, motion information in training engaged in based on the training information read at step S11 is read in. Next, at step S13, the read training information and the read motion information are compared. Next, at step S14, assessment information is generated based on the results of comparison at step S13 and the processing is ended.

Figure 35:
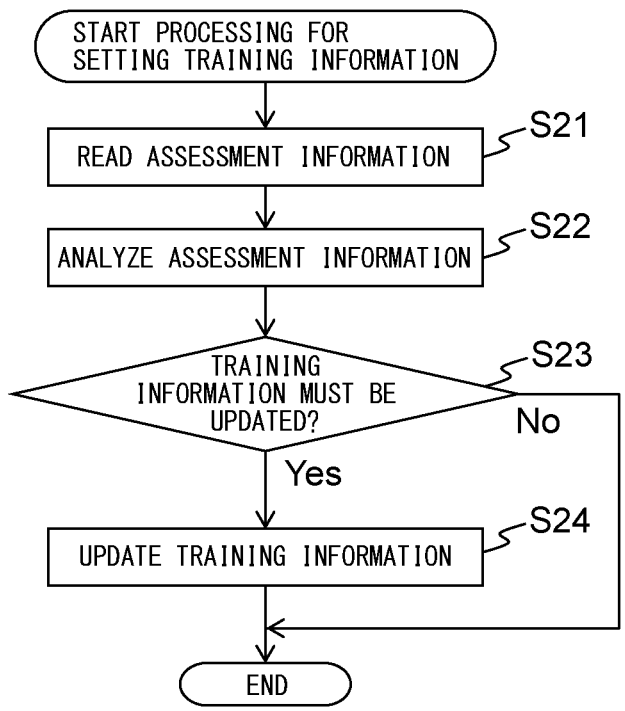
FIG. 35 is a flow chart of processing for setting training information.

FIG. 35 is a flow chart of processing for setting the training information. The processing for setting training information is performed by the training information setting part 73 of the central processing part 70.

Referring to FIG. 35, first, at step S21, the assessment information is read in. Next, at step S22, the assessment information is analyzed. Next, at step S23, it is judged if the training information has to be updated. If the training information does not have to be updated, the processing is ended. On the other hand, if the training information has to be updated, the routine proceeds to step S24. At step S24, the training information is generated and stored, that is, is updated, and the processing is ended.

Figure 36:
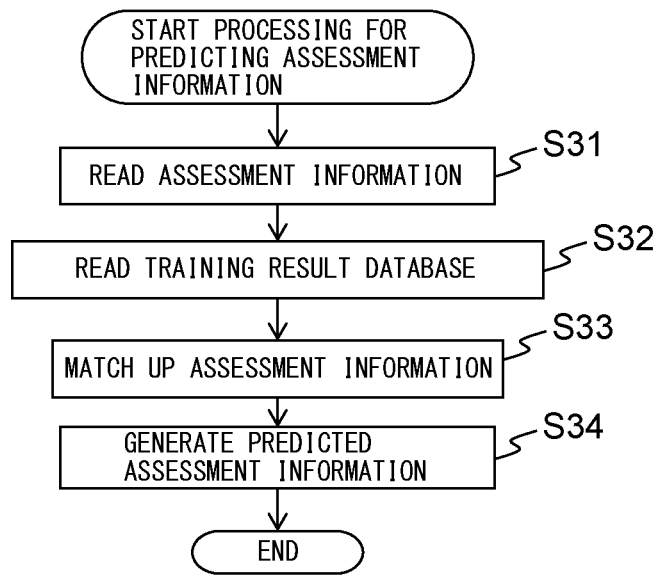
FIG. 36 is a flow chart of processing for predicting assessment information.

FIG. 36 is a flow chart of processing for predicting assessment information. The processing for predicting assessment information is performed by the assessment information predicting part 74 of the central processing part 70.

Referring to FIG. 36, first, at step S31, the assessment information of the patient at the present point of time is read in. Next, at step S32, the training result database is read in. Next, at step S33, the assessment information is matched. Next, at step S34, predicted assessment information is generated and the processing is ended.

Figure 37:
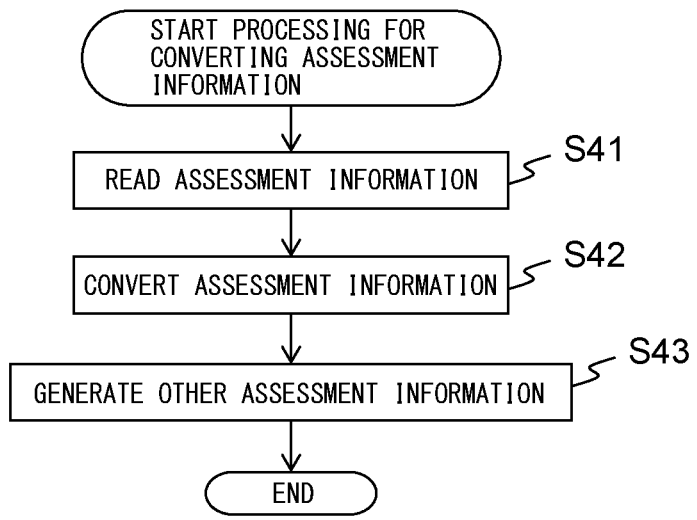
FIG. 37 is a flow chart of processing for converting assessment information.

FIG. 37 is a flow chart of processing for converting assessment information. The processing for converting assessment information is performed by the assessment information converting part 75 of the central processing part 70.

Referring to FIG. 37, first, at step S41, the assessment information is read in. Next, at step S42, the assessment information is converted. Next, at step S43, other assessment information is generated and the processing is ended.

According to the rehabilitation support apparatus 1 according to the present invention, it is possible to engage in training by repeating correct motion accurately and safely and in suitable amounts without being limited by fatigue of the therapist or upper limit on rehabilitation time in medical insurance systems. As a result, the load on the therapist can be lightened and the therapist can focus on fine tuned training. Further, a single therapist can handle a large number of patients.

Further, by selectively using training modes, training can be performed regardless of the condition of the patient, that is, by both mild case patients and severe case patients, using a single rehabilitation support apparatus 1. Further, entering the settings at that time and changing settings are also easy. Further, the training content can be standardized without relying upon the experience and skill of the therapist, so the medical quality of rehabilitation can also be standardized. The extent of restoration of the motion functions of the patients can also be made uniform.

Further, according to the rehabilitation support apparatus 1, motor functions can be simultaneously assessed during training and motor functions can be assessed objectively and without variation. Further, the assessment of motor functions can be confirmed at any time by graphs etc., so the motivation of the patient can be maintained. Furthermore, the rehabilitation support apparatus 1 enables training even without a medical practitioner close by, so training can be performed autonomously at the convenience of the patient. Furthermore, according to the rehabilitation support apparatus 1, it becomes possible to select the suitable training program semi-automatically or fully automatically in accordance with the condition of the patient.

In the above-mentioned embodiments, the rehabilitation support apparatus 1 was configured to deal with patients with impairment of their upper extremities, but the arm part may also be configured to deal with patients with impairment of their lower extremities. Furthermore, the arm part can also be configured to make the rehabilitation support apparatus 1 deal with parts other than the arm such as the wrist, elbow, shoulder, knee, etc.

Further, the rehabilitation support apparatus 1 according to the present invention may be used for various training applications. For example, it can be applied to not only prevention of adhesion and contracture of the joints of the upper extremities and improvement of the ranges of motion of joints, but also alleviation of pain, alleviation of muscle tension, improvement of sitting balance, improvement of motion awareness, strengthening of muscles of upper extremities, etc.

REFERENCE SIGNS LIST 1. rehabilitation support apparatus
20. holding part
30. arm part
40. display part
61. motion information acquiring part
72. motion assessing part
80. storage part

The invention claimed is:

1. A rehabilitation support apparatus, comprising:
an arm part having a holding part for holding part of an upper extremity or lower extremity of a user and supporting the holding part to be able to move,
a storage part storing training information, which storage part storing predetermined first training information,
a motion information acquiring part acquiring motion information accompanying movement of said holding part, said motion information acquiring part acquiring first motion information of said holding part moved based on said first training information,
a motion assessing part generating assessment information assessing said motion information, said motion assessing part assessing said first motion information and generating first assessment information,
a display part displaying at least one of said training information, said motion information, and said assessment information, and
an assessment information predicting part predicting assessment information of the user based on a plurality of said assessment information of users and generating predicted assessment information,
wherein said display part displays said predicted assessment information.

2. The rehabilitation support apparatus according to claim 1, wherein said motion assessing part generates said first assessment information based on a comparison of said first training information and said first motion information.

3. The rehabilitation support apparatus according to claim 1, further comprising a training information setting part generating next training information based on said assessment information and storing said training information in said storage part and, characterized by said training information setting part generating second training information based on said first assessment information and storing said second training information in said storage part.

4. The rehabilitation support apparatus according to claim 3, wherein said motion information acquiring part acquires second motion information of said holding part moved based on said second training information, said motion assessing part assesses said second motion information to generate second assessment information, and said training information setting part generates said second training information based on said first assessment information and/or said second assessment information.

5. The rehabilitation support apparatus according to claim 3, wherein said training information setting part generates said training information by selecting it from a predetermined plurality of said training information in said storage part.

6. The rehabilitation support apparatus according to claim 3, further comprising an interface part for entering initial assessment information on the motor functions of the user and, wherein said training information setting part generates said first training information based on said initial assessment information and stores said first training information in said storage part.

7. The rehabilitation support apparatus according to claim 1, wherein said display part displays said motion information in real time in accordance with movement of said holding part.

8. The rehabilitation support apparatus according to claim 1, wherein said arm part has a support point at one end and can move with at least one degree of freedom from said support point.

9. The rehabilitation support apparatus according to claim 1, wherein said training information and said motion information include at least one among a position of said holding part, a movement time of said holding part, a speed of said holding part, an acceleration of said holding part, and a force applied to said holding part.

10. The rehabilitation support apparatus according to claim 1, wherein said display part displays at least one of said training information and said assessment information.

11. The rehabilitation support apparatus according to claim 1, further comprising an assessment information converting part converting said assessment information to corresponding other assessment information or converting said corresponding other assessment information to said assessment information.

12. The rehabilitation support apparatus according to claim 11, wherein said other assessment information is shown by assessment items according to Fugl-Meyer Assessment.

13. A control method for a rehabilitation support apparatus comprising an arm part having a holding part of an upper extremity or lower extremity of a user and supporting said holding part to be able to move, the control method comprising:
- a step of storing training information, which step storing predetermined training information,
- a step of acquiring motion information accompanying movement of said holding part, which step acquiring motion information of said holding part moved based on said training information,
- a step of generating assessment information assessing said motion information, which step assessing said motion information and generating assessment information,
- a step of displaying at least one of said training information, said motion information, and said assessment information, and
- a step of predicting assessment information of the user based on a plurality of said assessment information of users and generating predicted assessment information, wherein the step of displaying includes displaying said predicted assessment information.

14. The rehabilitation support apparatus according to claim 1, wherein the display part displays said first training information, and said display part displays said first motion information, which was acquired based on said first training information, in real time.

15. The rehabilitation support apparatus according to claim 14, wherein said first training information corresponds to an ideal trajectory of said holding part, and said first motion information corresponds to an actual trajectory of said holding part.

16. The control method according to claim 13, wherein the step of displaying includes displaying said predetermined training information, and displaying said motion information in real time.

17. The control method according to claim 16, wherein said predetermined training information corresponds to an ideal trajectory of said holding part, and said motion information corresponds to an actual trajectory of said holding part.

* * * * *